(12) United States Patent
Jaenisch et al.

(10) Patent No.: US 9,267,123 B2
(45) Date of Patent: Feb. 23, 2016

(54) METHODS AND COMPOSITIONS FOR GENE CORRECTION

(75) Inventors: Rudolf Jaenisch, Brookline, MA (US); Josee Laganiere, El Cerrito, CA (US); Frank Soldner, Cambridge, MA (US); Lei Zhang, Davis, CA (US)

(73) Assignees: Sangamo BioSciences, Inc., Richmond, CA (US); Whitehead Institute for Biomedical Research, Cambridge, MA (US)

( * ) Notice: Subject to any disclaimer, the term of this patent is extended or adjusted under 35 U.S.C. 154(b) by 1014 days.

(21) Appl. No.: 13/327,558

(22) Filed: Dec. 15, 2011

(65) Prior Publication Data

US 2012/0192301 A1    Jul. 26, 2012

Related U.S. Application Data

(60) Provisional application No. 61/460,686, filed on Jan. 5, 2011, provisional application No. 61/517,478, filed on Apr. 20, 2011.

(51) Int. Cl.
C12N 9/22    (2006.01)

(52) U.S. Cl.
CPC .............. *C12N 9/22* (2013.01); *C07K 2319/00* (2013.01); *C07K 2319/81* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |

(Continued)

FOREIGN PATENT DOCUMENTS

| | | |
|---|---|---|
| GB | 2338237 | 12/1999 |
| WO | WO 95/19431 A1 | 7/1995 |

(Continued)

OTHER PUBLICATIONS

Gandhi et al., "Leucine-rich repeat kinase 2 (LRRK2): A key player in the pathogenesis of Parkinson's disease", Journal of Neuroscience Research, vol. 87, pp. 1283-1295, 2009.*

(Continued)

*Primary Examiner* — Robert Mondesi
*Assistant Examiner* — Richard Ekstrom
(74) *Attorney, Agent, or Firm* — Pasternak Patent Law; Dahna S. Pasternak

(57) ABSTRACT

Disclosed herein are methods and compositions for correction and/or mutation of genes associated with Parkinson's Disease as well as clones and animals derived therefrom.

2 Claims, 8 Drawing Sheets

(56) References Cited

U.S. PATENT DOCUMENTS

| | | | |
|---|---|---|---|
| 6,607,882 | B1 | 8/2003 | Cox, III et al. |
| 6,689,558 | B2 | 2/2004 | Case |
| 6,794,136 | B1 | 9/2004 | Eisenberg et al. |
| 6,824,978 | B1 | 11/2004 | Cox, III et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,030,215 | B2* | 4/2006 | Liu et al. ............... 530/333 |
| 7,067,317 | B2 | 6/2006 | Rebar et al. |
| 7,070,934 | B2 | 7/2006 | Cox, III et al. |
| 7,153,949 | B2 | 12/2006 | Kim et al. |
| 7,163,824 | B2 | 1/2007 | Cox, III et al. |
| 7,253,273 | B2 | 8/2007 | Collingwood |
| 7,262,054 | B2 | 8/2007 | Jaimeson et al. |
| 7,361,635 | B2 | 4/2008 | Miller et al. |
| 2002/0061512 | A1* | 5/2002 | Kim et al. .......................... 435/4 |
| 2003/0232410 | A1* | 12/2003 | Liljedahl et al. ............ 435/69.1 |
| 2005/0026157 | A1* | 2/2005 | Baltimore et al. ............... 435/6 |
| 2005/0064474 | A1* | 3/2005 | Urnov et al. ..................... 435/6 |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1* | 8/2006 | Guschin et al. ............... 435/455 |
| 2007/0134796 | A1* | 6/2007 | Holmes et al. ............... 435/455 |
| 2007/0218528 | A1* | 9/2007 | Miller .......................... 435/91.2 |
| 2008/0131962 | A1 | 6/2008 | Miller et al. |
| 2009/0068164 | A1 | 3/2009 | Segal et al. |
| 2011/0129898 | A1 | 6/2011 | Doyon |
| 2011/0201055 | A1 | 8/2011 | Doyon et al. |
| 2011/0287512 | A1 | 11/2011 | Paschon et al. |
| 2011/0301073 | A1 | 12/2011 | Gregory et al. |
| 2012/0192298 | A1* | 7/2012 | Weinstein et al. ............. 800/14 |
| 2012/0214241 | A1* | 8/2012 | Laganiere et al. ............ 435/462 |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077272 A2 | 10/2002 |
| WO | WO 02/099084 A2 | 12/2002 |
| WO | WO 03/016496 A2 | 2/2003 |
| WO | WO 2007/014275 A2 | 2/2007 |
| WO | WO 2009/005730 A1 | 1/2009 |
| WO | WO 2009/042163 A2 | 4/2009 |

OTHER PUBLICATIONS

Schule et al., "Can cellular models revolutionize drug discovery in Parkinson's disease?", Biochimica et Biophysica Acta, vol. 1792, pp. 1043-1051, 2009.*

Durai et al., "Zinc finger nucleases: custom-designed molecular scissors for genome engineering of plant and mammalian cells", Nucleic Acids Research, vol. 33, No. 18, pp. 5978-5990, 2005.*

Beerli, et al., "Engineering Polydactyl Zinc-Finger Transcription Factors," *Nature Biotechnol.* 20:135-141 (2002).

Belfort, et al., "Homing Endonucleases: Keeping the House in Order," *Nucl. Acids Res.* 25(17):3379-3388 (1997).

Bitinaite, et al., "FokI Dimerization Is Required for DNA Cleavage," *Proc. Natl. Acad. Sci.* 95(18):10570-10575 (1998).

Choo, et al., "Advances in Zinc Finger Engineering," *Curr. Opin. Struct. Biol.*, 10:411-416 (2000).

Davie, "A Review of Parkinson's Disease," *Br. Med. Bull.* 86(1):109-127 (2008).

Dawson, et al., "Genetic Animal Models of Parkinson's Disease," *Neuron* 66(5):646-661 (2010).

Gore, et al., "Somatic Coding Mutations in Human Induced Pluripotent Stem Cells," *Nature* 471(7336):63-67 (2011).

Guschin, et al., "A Rapid and General Assay for Monitoring Endogenous Gene Modification," *Meth. Mol. Biol.* 649:247-256 (2010).

Hockemeyer, et al., "A Drug-Inducible System for Direct Reprogramming of Human Somatic Cells to Pluripotency," *Cell Stem Cell* 3(3):346-353 (2008).

Hussein, et al., "Copy Number Variation and Selection During Reprogramming to Pluripotency," *Nature* 471 (7336):58-62 (2011).

Isalan, et al., "A Rapid, Generally Applicable Method to Engineer Zinc Fingers Illustrated by Targeting the HIV-1 Promoter," *Nature Biotechnology* 19(7):656-660 (2001).

Kim, et al., "Insertion and Deletion Mutants of FokI Restriction Endonuclease," *J. Biol. Chem.* 269(50):31978-31982 (1994).

Kim, et al., "Chimeric Restriction Endonuclease," *Proc. Natl. Acad. Sci.* 91(3):883-887 (1994).

Kim, et al., "Hybrid Restriction Enzymes: Zinc Finger Fusions to Fok I Cleavage Domain," *Proc. Natl. Acad. Sci.* 93(3):1156-1160 (1996).

Kumari, et al., "LRRK2 in Parkinson's Disease: Genetic and Clinical Studies From Patients," *Febs J.* 276(22):6455-6463 (2009).

Li, et al., "Functional Domains in Fok I Restriction Endonuclease," *Proc. Natl. Acad. Sci.* 89(10):4275-4279 (1992).

Li, et al., "Alteration of the Cleavage Distance of Fok I Restriction Endonuclease by Insertion Mutangensis," *Proc. Natl. Acad. Sci.* 90(7):2764-2768 (1993).

Luzon-Toro, et al., "Mechanistic Insight Into the Dominant Mode of the Parkinson's Diseaseassociated G2019S LRRK2 Mutation," *Hum. Mol. Genet.* 16(17):2031-2039 (2007).

Narva, et al., "High-Resolution DNA Analysis of Human Embryonic Stem Cell Lines Reveals Culture-Induced Copy Number Changes and Loss of Heterozygosity," *Nat. Biotechnol.* 28(4):371-377 (2010).

Pabo, et al., "Design and Selection of Novel CYS2HIS2 Zinc Finger Proteins," *Ann. Rev. Biochem.* 70:313-340 (2001).

Pankratz, et al., "Genetics of Parkinson Disease," *NeuroRx®: The Journal of the American Society for Experimental NeuroTherapeutics* 1:235-242 (2004).

Perez, et al., "Establishment of HIV-1 Resistance in CD4+ T Cells by Genome Editing Using Zinc-Finger Nucleases," *Nat. Biotechnol.* 26(7):808-816 (2008).

Pirkevi, et al., "From Genes to Proteins in Mendelian Parkinson's Disease: An Overview," *The Anatomical Record* 292(12):1893-1901 (2009).

Segal, et al., "Custom DNA-Binding Proteins Come of Age: Polydactyl Zinc-Finger Proteins," *Curr. Opin. Biotechnol.* 12(6):632-637 (2001).

Singleton, et al., "A-Synuclein Locus Triplication Causes Parkinson's Disease," *Science* 302(5646):841 (2003).

Soldner, et al., "Parkinson's Disease Patient-Derived Induced Pluripotent Stem Cells Free of Viral Reprogramming Factors," *Cell* 136(5):964-977 (2009).

Soldner, et al., "Generation of Isogenic Pluripotent Stem Cells Differing Exclusively at Two Early Onset Parkinson Point Mutations," *Cell* 146(2):318-331 (2011).

Winslow, et al., "The Parkinson Disease Protein A-Synuclein Inhibits Autophagy," *Autophagy* 7(4):429-431(2011).

* cited by examiner

SEQUENCE LISTING

```
<160> NUMBER OF SEQ ID NOS: 59

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Gly Asp Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Asn Asp Ile Leu Ala Ser
1               5

<210> SEQ ID NO 3
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Arg Ser Asn Leu Ser Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Gln Asp Leu Lys Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ser Gly Asn Leu Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Asn Gln Leu Arg Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Gly His Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Arg Ser Asp Ser Leu Ser Val
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Asp Leu Arg Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Lys Asp Pro Leu Lys Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Asp Pro Leu Ile Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Gly His Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Lys Trp Thr Leu Gln Gly
1               5

<210> SEQ ID NO 14
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 14

Gln Ser Ser Asp Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Trp Ser Thr Arg Lys Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Ala Leu Thr Gln
1               5

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcaaagattg ctgactacgg cattgctc                                        28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgatggcagc attgggatac agtgtgaa                                        28

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Arg Asp Tyr Leu Ile Lys
1               5

<210> SEQ ID NO 20
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Pro Tyr Thr Leu Arg Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Arg Ser Asp Arg Thr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Gly Ala Leu Ala Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Asn Leu Arg Glu
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Lys Arg Asn Arg Thr Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ser Ser Asp Arg Lys Lys
```

```
<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Gln Ser Asn Leu Arg Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ser His Asn Leu Arg Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Ser His Asn Arg Asn Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Arg Ser Tyr Arg Asn Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ser Asn Asp Leu Asn Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 31

Thr Ser Gly Ser Leu Ser Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Arg Ser Ser Leu Thr Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Arg Asp Ser Leu Ile Glu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Ser Asp Leu Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Arg Ser Asn Arg Lys Thr
1               5

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aacaggtaag ctccattgtg cttatatc                                        28

<210> SEQ ID NO 37
<211> LENGTH: 28

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cacaccatgc accactccct ccttggtt                                           28

<210> SEQ ID NO 38
<211> LENGTH: 998
<212> TYPE: DNA
<213> ORGANISM: Homo sapiens

<400> SEQUENCE: 38
agctgagcta aacctctatg tggttttagg aaaatcaaaa ctattaaata aatggcaagt         60
acaacaaaat cccatcaatt cttatttaac atacttacat tttgaaatag ttaaaatatt        120
catatgatca ttgagagaat tcagaattgc ctttaagtaa ttgttcacat atacaaaaga        180
aaagtctcca aaaattgggt ctttgcctga gatagatttg tcttaaaatt gaaatcattc        240
acttatcaga tttgacccct ttttaaagca taactttgct gtgtaatatt agacttatat        300
gttttgattt ccttctacaa tatctcttaa ctttaagggga caaagtgagc acagaatttt      360
tgatgcttga catagtggac atttatattt aaggaaatta ggacaaaaat tattataatg        420
taatcacatt tgaataagat ttcctgtgca ttttctggca gatacctcca ctcagccatg        480
attatatacc gagacctgaa accccacaat gtgctgcttt tcacactgta tcccaatgct        540
gccatcattg caaagattgc tgactacagc attgctcagt actgctgtag aatggggata        600
aaaacatcag agggcacacc aggtaggtga tcaggtctgt ctcataattc tatcttcagg        660
atggataacc actgacctca gatgtgagtt cagaagagtc aaaaggaaaa cagagtctat        720
cacattgtga acagaggttt attttgtgaa aaaatgcaag catcacattg tgatttttat        780
cattgtattt tgtaggaaaa aaacaattga tgtaattttt cagggcaaaa actgaataaa        840
aagaagagaa tgtttgatat caagttatat gttttaaagt tagatttgta gattctttag        900
atactctaga ggtcataaaa agtaacagca aaaactttag tctaggtatt gttggcactt        960
gtgaggcaaa tcaaattcag gtccacaaat tcttttttc                                998

<210> SEQ ID NO 39
<211> LENGTH: 1023
<212> TYPE: DNA
<213> ORGANISM: Homo sapiens

<400> SEQUENCE: 39
ctcgtgatct gcccacctcg gcctcccaaa ttgctgggat tacaggcatg agccactgcg         60
cccagcctaa aatgtttttt ttacataatg ggtgttcagc acatgttaaa gccttctctc        120
catccttctt ccctttttgtt tcatgggttg actgatctgt ctctagtgct gtacttttaa       180
agcttctaca gttctgaatt caaaattatc ttctcactgg gccccggtgt tatctcattc        240
ttttttctcc tctgtaagtt gacatgtgat gtgggaacaa aggggataaa gtcattattt        300
tgtgctaaaa tcgtaattgg agaggacctc ctgttagctg ggctttcttc tatttattgt        360
ggtggttact ggagttcctt cttctagttt taggatatat atatatattt ttttctttcc        420
ctgaagatat aataatatat atacttctga agattgagat ttttaaatta gttgtattga        480
aaactagcta atcagcaatt taaggctagc ttgagactta tgtcttgaat ttgttttttgt       540 aggctccaaa accaaggagg gagtggtgca tggtgtgaca acaggtaagc tccattgtgc        600
```

```
ttatatccaa agatgatatt taaagtatct agtgattagt gtggcccagt attcaagatt    660
cctatgaaat tgtaaaacaa tcactgagca ttctaagaac atatcagtct tattgaaact    720
gaattcttta taaagtattt ttaaataggt aaatattgat tataaataaa aaatatactt    780
gccaagaata atgagggctt tgaattgata agctatgttt aatttatagt aagtgggcat    840
ttaaatattc tgaccaaaaa tgtattgaca aactgctgac aaaaataaaa tgtgaatatt    900
gccataattt taaaaaaagt aaaatttctg ttgattacag taaaatattt tgaccttaaa    960
ttatgttgat tacaatattc ctttgataat tcagagtgca tttcaggaaa caccccttgga   1020 cag                                                                  1023
```

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
aagattccca tatcattgtc ctc                                              23
```

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ggtttggaag aaattctgat cctg                                             24
```

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
aaactagcta atcagcaatt taaggc                                           26
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
agccctcatt attcttggca                                                  20
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Ser Leu Ser Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Trp Gly Thr Arg Tyr Arg
1               5

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcaaagattg ctgactacag cattgctc                                       28

<210> SEQ ID NO 47
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cttttcacac tgtatcccaa tgctgccatc attgcaaaga ttgctgacta cagcattgct    60
cagtact                                                              67

<210> SEQ ID NO 48
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agtactgagc aatgctgtag tcagcaatct ttgcaatgat ggcagcattg ggatacagtg    60
tgaaaag                                                              67

<210> SEQ ID NO 49
<211> LENGTH: 67
<212> TYPE: DNA
<213> ORGANISM: Homo sapiens

<400> SEQUENCE: 49
cttttcacac tgtatcccaa tgctgccatc attgcaaaga ttgctgacta cggcattgct    60
cagtact                                                              67

<210> SEQ ID NO 50
<211> LENGTH: 67
<212> TYPE: DNA
<213> ORGANISM: Homo sapiens

<400> SEQUENCE: 50
agtactgagc aatgccgtag tcagcaatct ttgcaatgat ggcagcattg ggatacagtg    60
tgaaaag                                                               67

<210> SEQ ID NO 51
<211> LENGTH: 6
<212> TYPE: PRT
<213> ORGANISM: Homo sapiens

<400> SEQUENCE: 51

Lys Thr Lys Glu Gly Val
1               5

<210> SEQ ID NO 52
<211> LENGTH: 110
<212> TYPE: DNA
<213> ORGANISM: Homo sapiens

<400> SEQUENCE: 52
agacttatgt cttgaatttg tttttgtagg ctccaaaacc aaggagggag tggtgcatgg    60
tgtggcaaca ggtaagctcc attgtgctta tatccaaaga tgatatttaa              110

<210> SEQ ID NO 53
<211> LENGTH: 79
<212> TYPE: PRT
<213> ORGANISM: Homo sapiens

<400> SEQUENCE: 53

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln
65                  70                  75

<210> SEQ ID NO 54
<211> LENGTH: 79
<212> TYPE: PRT
<213> ORGANISM: Homo sapiens

<400> SEQUENCE: 54

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln
65                  70                  75

<210> SEQ ID NO 55
<211> LENGTH: 79
<212> TYPE: PRT

<213> ORGANISM: Homo sapiens

<400> SEQUENCE: 55

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Lys Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln
65                  70                  75
```

<210> SEQ ID NO 56
<211> LENGTH: 2527
<212> TYPE: PRT
<213> ORGANISM: Homo sapiens

<400> SEQUENCE: 56

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
            35                  40                  45

Glu His Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
```

```
                    275                 280                 285
Asn Glu Val His Glu Phe Val Lys Ala Val Gln Gln Tyr Pro Glu
            290                 295                 300
Asn Ala Ala Leu Gln Ile Ser Ala Leu Ser Cys Leu Ala Leu Leu Thr
305                 310                 315                 320
Glu Thr Ile Phe Leu Asn Gln Asp Leu Glu Lys Asn Glu Asn Gln
                325                 330                 335
Glu Asn Asp Asp Glu Gly Glu Asp Lys Leu Phe Trp Leu Glu Ala
            340                 345                 350
Cys Tyr Lys Ala Leu Thr Trp His Arg Lys Asn Lys His Val Gln Glu
                355                 360                 365
Ala Ala Cys Trp Ala Leu Asn Asn Leu Leu Met Tyr Gln Asn Ser Leu
370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
                    405                 410                 415
Ala Ser Ala Asn Ala Leu Ser Thr Leu Leu Glu Gln Asn Val Asn Phe
                420                 425                 430
Arg Lys Ile Leu Leu Ser Lys Gly Ile His Leu Asn Val Leu Glu Leu
            435                 440                 445
Met Gln Lys His Ile His Ser Pro Glu Val Ala Glu Ser Gly Cys Lys
    450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
                    485                 490                 495
Ser Leu Pro Val Gln Leu Glu Ala Leu Arg Ala Ile Leu His Phe Ile
                500                 505                 510
Val Pro Gly Met Pro Glu Glu Ser Arg Glu Asp Thr Glu Phe His His
            515                 520                 525
Lys Leu Asn Met Val Lys Lys Gln Cys Phe Lys Asn Asp Ile His Lys
    530                 535                 540
Leu Val Leu Ala Ala Leu Asn Arg Phe Ile Gly Asn Pro Gly Ile Gln
545                 550                 555                 560
Lys Cys Gly Leu Lys Val Ile Ser Ser Ile Val His Phe Pro Asp Ala
                565                 570                 575
Leu Glu Met Leu Ser Leu Glu Gly Ala Met Asp Ser Val Leu His Thr
            580                 585                 590
Leu Gln Met Tyr Pro Asp Asp Gln Glu Ile Gln Cys Leu Gly Leu Ser
    595                 600                 605
Leu Ile Gly Tyr Leu Ile Thr Lys Lys Asn Val Phe Ile Gly Thr Gly
610                 615                 620
His Leu Leu Ala Lys Ile Leu Val Ser Ser Leu Tyr Arg Phe Lys Asp
625                 630                 635                 640
Val Ala Glu Ile Gln Thr Lys Gly Phe Gln Thr Ile Leu Ala Ile Leu
                645                 650                 655
Lys Leu Ser Ala Ser Phe Ser Lys Leu Leu Val His His Ser Phe Asp
                660                 665                 670
Leu Val Ile Phe His Gln Met Ser Ser Asn Ile Met Glu Gln Lys Asp
            675                 680                 685
Gln Gln Phe Leu Asn Leu Cys Cys Lys Cys Phe Ala Lys Val Ala Met
    690                 695                 700
```

```
Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
            725                 730                 735

Gln Ala Lys Glu Gly Ser Ser Leu Ile Cys Gln Val Cys Glu Lys Glu
        740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
        770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
            805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
            885                 890                 895

Gly Ser Glu Gly Ser Phe Leu Val Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
        930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
        995                 1000                1005

His Leu Glu His Leu Glu Lys Leu Glu Leu His Gln Asn Ala Leu
        1010                1015                1020

Thr Ser Phe Pro Gln Gln Leu Cys Glu Thr Leu Lys Ser Leu Thr
        1025                1030                1035

His Leu Asp Leu His Ser Asn Lys Phe Thr Ser Phe Pro Ser Tyr
        1040                1045                1050

Leu Leu Lys Met Ser Cys Ile Ala Asn Leu Asp Val Ser Arg Asn
        1055                1060                1065

Asp Ile Gly Pro Ser Val Val Leu Asp Pro Thr Val Lys Cys Pro
        1070                1075                1080

Thr Leu Lys Gln Phe Asn Leu Ser Tyr Asn Gln Leu Ser Phe Val
        1085                1090                1095

Pro Glu Asn Leu Thr Asp Val Val Glu Lys Leu Glu Gln Leu Ile
        1100                1105                1110
```

-continued

```
Leu Glu Gly Asn Lys Ile Ser Gly Ile Cys Ser Pro Leu Arg Leu
    1115                1120                1125
Lys Glu Leu Lys Ile Leu Asn Leu Ser Lys Asn His Ile Ser Ser
    1130                1135                1140
Leu Ser Glu Asn Phe Leu Glu Ala Cys Pro Lys Val Glu Ser Phe
    1145                1150                1155
Ser Ala Arg Met Asn Phe Leu Ala Ala Met Pro Phe Leu Pro Pro
    1160                1165                1170
Ser Met Thr Ile Leu Lys Leu Ser Gln Asn Lys Phe Ser Cys Ile
    1175                1180                1185
Pro Glu Ala Ile Leu Asn Leu Pro His Leu Arg Ser Leu Asp Met
    1190                1195                1200
Ser Ser Asn Asp Ile Gln Tyr Leu Pro Gly Pro Ala His Trp Lys
    1205                1210                1215
Ser Leu Asn Leu Arg Glu Leu Leu Phe Ser His Asn Gln Ile Ser
    1220                1225                1230
Ile Leu Asp Leu Ser Glu Lys Ala Tyr Leu Trp Ser Arg Val Glu
    1235                1240                1245
Lys Leu His Leu Ser His Asn Lys Leu Lys Glu Ile Pro Pro Glu
    1250                1255                1260
Ile Gly Cys Leu Glu Asn Leu Thr Ser Leu Asp Val Ser Tyr Asn
    1265                1270                1275
Leu Glu Leu Arg Ser Phe Pro Asn Glu Met Gly Lys Leu Ser Lys
    1280                1285                1290
Ile Trp Asp Leu Pro Leu Asp Glu Leu His Leu Asn Phe Asp Phe
    1295                1300                1305
Lys His Ile Gly Cys Lys Ala Lys Asp Ile Ile Arg Phe Leu Gln
    1310                1315                1320
Gln Arg Leu Lys Lys Ala Val Pro Tyr Asn Arg Met Lys Leu Met
    1325                1330                1335
Ile Val Gly Asn Thr Gly Ser Gly Lys Thr Thr Leu Leu Gln Gln
    1340                1345                1350
Leu Met Lys Thr Lys Lys Ser Asp Leu Gly Met Gln Ser Ala Thr
    1355                1360                1365
Val Gly Ile Asp Val Lys Asp Trp Pro Ile Gln Ile Arg Asp Lys
    1370                1375                1380
Arg Lys Arg Asp Leu Val Leu Asn Val Trp Asp Phe Ala Gly Arg
    1385                1390                1395
Glu Glu Phe Tyr Ser Thr His Pro His Phe Met Thr Gln Arg Ala
    1400                1405                1410
Leu Tyr Leu Ala Val Tyr Asp Leu Ser Lys Gly Gln Ala Glu Val
    1415                1420                1425
Asp Ala Met Lys Pro Trp Leu Phe Asn Ile Lys Ala Arg Ala Ser
    1430                1435                1440
Ser Ser Pro Val Ile Leu Val Gly Thr His Leu Asp Val Ser Asp
    1445                1450                1455
Glu Lys Gln Arg Lys Ala Cys Met Ser Lys Ile Thr Lys Glu Leu
    1460                1465                1470
Leu Asn Lys Arg Gly Phe Pro Ala Ile Arg Asp Tyr His Phe Val
    1475                1480                1485
Asn Ala Thr Glu Glu Ser Asp Ala Leu Ala Lys Leu Arg Lys Thr
    1490                1495                1500
Ile Ile Asn Glu Ser Leu Asn Phe Lys Ile Arg Asp Gln Leu Val
```

-continued

```
            1505                1510                1515
Val Gly Gln Leu Ile Pro Asp Cys Tyr Val Glu Leu Glu Lys Ile
    1520                1525                1530
Ile Leu Ser Glu Arg Lys Asn Val Pro Ile Glu Phe Pro Val Ile
    1535                1540                1545
Asp Arg Lys Arg Leu Leu Gln Leu Val Arg Glu Asn Gln Leu Gln
    1550                1555                1560
Leu Asp Glu Asn Glu Leu Pro His Ala Val His Phe Leu Asn Glu
    1565                1570                1575
Ser Gly Val Leu Leu His Phe Gln Asp Pro Ala Leu Gln Leu Ser
    1580                1585                1590
Asp Leu Tyr Phe Val Glu Pro Lys Trp Leu Cys Lys Ile Met Ala
    1595                1600                1605
Gln Ile Leu Thr Val Lys Val Glu Gly Cys Pro Lys His Pro Lys
    1610                1615                1620
Gly Ile Ile Ser Arg Arg Asp Val Glu Lys Phe Leu Ser Lys Lys
    1625                1630                1635
Arg Lys Phe Pro Lys Asn Tyr Met Thr Gln Tyr Phe Lys Leu Leu
    1640                1645                1650
Glu Lys Phe Gln Ile Ala Leu Pro Ile Gly Glu Glu Tyr Leu Leu
    1655                1660                1665
Val Pro Ser Ser Leu Ser Asp His Arg Pro Val Ile Glu Leu Pro
    1670                1675                1680
His Cys Glu Asn Ser Glu Ile Ile Ile Arg Leu Tyr Glu Met Pro
    1685                1690                1695
Tyr Phe Pro Met Gly Phe Trp Ser Arg Leu Ile Asn Arg Leu Leu
    1700                1705                1710
Glu Ile Ser Pro Tyr Met Leu Ser Gly Arg Glu Arg Ala Leu Arg
    1715                1720                1725
Pro Asn Arg Met Tyr Trp Arg Gln Gly Ile Tyr Leu Asn Trp Ser
    1730                1735                1740
Pro Glu Ala Tyr Cys Leu Val Gly Ser Glu Val Leu Asp Asn His
    1745                1750                1755
Pro Glu Ser Phe Leu Lys Ile Thr Val Pro Ser Cys Arg Lys Gly
    1760                1765                1770
Cys Ile Leu Leu Gly Gln Val Val Asp His Ile Asp Ser Leu Met
    1775                1780                1785
Glu Glu Trp Phe Pro Gly Leu Leu Glu Ile Asp Ile Cys Gly Glu
    1790                1795                1800
Gly Glu Thr Leu Leu Lys Lys Trp Ala Leu Tyr Ser Phe Asn Asp
    1805                1810                1815
Gly Glu Glu His Gln Lys Ile Leu Leu Asp Asp Leu Met Lys Lys
    1820                1825                1830
Ala Glu Glu Gly Asp Leu Leu Val Asn Pro Asp Gln Pro Arg Leu
    1835                1840                1845
Thr Ile Pro Ile Ser Gln Ile Ala Pro Asp Leu Ile Leu Ala Asp
    1850                1855                1860
Leu Pro Arg Asn Ile Met Leu Asn Asn Asp Glu Leu Glu Phe Glu
    1865                1870                1875
Gln Ala Pro Glu Phe Leu Leu Gly Asp Gly Ser Phe Gly Ser Val
    1880                1885                1890
Tyr Arg Ala Ala Tyr Glu Gly Glu Glu Val Ala Val Lys Ile Phe
    1895                1900                1905
```

```
Asn Lys His Thr Ser Leu Arg Leu Leu Arg Gln Glu Leu Val Val
    1910            1915                1920

Leu Cys His Leu His His Pro Ser Leu Ile Ser Leu Leu Ala Ala
    1925            1930                1935

Gly Ile Arg Pro Arg Met Leu Val Met Glu Leu Ala Ser Lys Gly
    1940            1945                1950

Ser Leu Asp Arg Leu Leu Gln Gln Asp Lys Ala Ser Leu Thr Arg
    1955            1960                1965

Thr Leu Gln His Arg Ile Ala Leu His Val Ala Asp Gly Leu Arg
    1970            1975                1980

Tyr Leu His Ser Ala Met Ile Ile Tyr Arg Asp Leu Lys Pro His
    1985            1990                1995

Asn Val Leu Leu Phe Thr Leu Tyr Pro Asn Ala Ala Ile Ile Ala
    2000            2005                2010

Lys Ile Ala Asp Tyr Ser Ile Ala Gln Tyr Cys Cys Arg Met Gly
    2015            2020                2025

Ile Lys Thr Ser Glu Gly Thr Pro Gly Phe Arg Ala Pro Glu Val
    2030            2035                2040

Ala Arg Gly Asn Val Ile Tyr Asn Gln Gln Ala Asp Val Tyr Ser
    2045            2050                2055

Phe Gly Leu Leu Leu Tyr Asp Ile Leu Thr Thr Gly Gly Arg Ile
    2060            2065                2070

Val Glu Gly Leu Lys Phe Pro Asn Glu Phe Asp Glu Leu Glu Ile
    2075            2080                2085

Gln Gly Lys Leu Pro Asp Pro Val Lys Glu Tyr Gly Cys Ala Pro
    2090            2095                2100

Trp Pro Met Val Glu Lys Leu Ile Lys Gln Cys Leu Lys Glu Asn
    2105            2110                2115

Pro Gln Glu Arg Pro Thr Ser Ala Gln Val Phe Asp Ile Leu Asn
    2120            2125                2130

Ser Ala Glu Leu Val Cys Leu Thr Arg Arg Ile Leu Leu Pro Lys
    2135            2140                2145

Asn Val Ile Val Glu Cys Met Val Ala Thr His His Asn Ser Arg
    2150            2155                2160

Asn Ala Ser Ile Trp Leu Gly Cys Gly His Thr Asp Arg Gly Gln
    2165            2170                2175

Leu Ser Phe Leu Asp Leu Asn Thr Glu Gly Tyr Thr Ser Glu Glu
    2180            2185                2190

Val Ala Asp Ser Arg Ile Leu Cys Leu Ala Leu Val His Leu Pro
    2195            2200                2205

Val Glu Lys Glu Ser Trp Ile Val Ser Gly Thr Gln Ser Gly Thr
    2210            2215                2220

Leu Leu Val Ile Asn Thr Glu Asp Gly Lys Lys Arg His Thr Leu
    2225            2230                2235

Glu Lys Met Thr Asp Ser Val Thr Cys Leu Tyr Cys Asn Ser Phe
    2240            2245                2250

Ser Lys Gln Ser Lys Gln Lys Asn Phe Leu Leu Val Gly Thr Ala
    2255            2260                2265

Asp Gly Lys Leu Ala Ile Phe Glu Asp Lys Thr Val Lys Leu Lys
    2270            2275                2280

Gly Ala Ala Pro Leu Lys Ile Leu Asn Ile Gly Asn Val Ser Thr
    2285            2290                2295
```

Pro Leu Met Cys Leu Ser Glu Ser Thr Asn Ser Thr Glu Arg Asn
    2300                2305                2310

Val Met Trp Gly Gly Cys Gly Thr Lys Ile Phe Ser Phe Ser Asn
    2315                2320                2325

Asp Phe Thr Ile Gln Lys Leu Ile Glu Thr Arg Thr Ser Gln Leu
    2330                2335                2340

Phe Ser Tyr Ala Ala Phe Ser Asp Ser Asn Ile Ile Thr Val Val
    2345                2350                2355

Val Asp Thr Ala Leu Tyr Ile Ala Lys Gln Asn Ser Pro Val Val
    2360                2365                2370

Glu Val Trp Asp Lys Lys Thr Glu Lys Leu Cys Gly Leu Ile Asp
    2375                2380                2385

Cys Val His Phe Leu Arg Glu Val Thr Val Lys Glu Asn Lys Glu
    2390                2395                2400

Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly Gly His
    2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
    2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
    2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
    2510                2515                2520

Thr Ser Val Glu
    2525

<210> SEQ ID NO 57
<211> LENGTH: 2527
<212> TYPE: PRT
<213> ORGANISM: Homo sapiens

<400> SEQUENCE: 57

Met Ala Ser Gly Ser Cys Gln Gly Cys Glu Glu Asp Glu Thr Leu
1               5                   10                  15

Lys Lys Leu Ile Val Arg Leu Asn Asn Val Gln Glu Gly Lys Gln Ile
                20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

```
Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
                180                 185                 190

Glu Glu Gln Leu Thr Glu Phe Val Glu Asn Lys Asp Tyr Met Ile Leu
                195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260                 265                 270

Leu Leu His Arg Leu Thr Leu Gly Asn Phe Phe Asn Ile Leu Val Leu
                275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
                340                 345                 350

Cys Tyr Lys Ala Leu Thr Trp His Arg Lys Asn Lys His Val Gln Glu
                355                 360                 365

Ala Ala Cys Trp Ala Leu Asn Asn Leu Leu Met Tyr Gln Asn Ser Leu
                370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
                435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
                515                 520                 525

Lys Leu Asn Met Val Lys Lys Gln Cys Phe Lys Asn Asp Ile His Lys
530                 535                 540
```

```
Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
```

```
            965                 970                 975
Leu Ala Ser Glu Arg Glu Tyr Ile Thr Ser Leu Asp Leu Ser Ala Asn
            980                 985                 990
Glu Leu Arg Asp Ile Asp Ala Leu Ser Gln Lys Cys Cys Ile Ser Val
            995                 1000                1005
His Leu Glu His Leu Glu Lys Leu Glu Leu His Gln Asn Ala Leu
            1010                1015                1020
Thr Ser Phe Pro Gln Gln Leu Cys Glu Thr Leu Lys Ser Leu Thr
            1025                1030                1035
His Leu Asp Leu His Ser Asn Lys Phe Thr Ser Phe Pro Ser Tyr
            1040                1045                1050
Leu Leu Lys Met Ser Cys Ile Ala Asn Leu Asp Val Ser Arg Asn
            1055                1060                1065
Asp Ile Gly Pro Ser Val Val Leu Asp Pro Thr Val Lys Cys Pro
            1070                1075                1080
Thr Leu Lys Gln Phe Asn Leu Ser Tyr Asn Gln Leu Ser Phe Val
            1085                1090                1095
Pro Glu Asn Leu Thr Asp Val Val Glu Lys Leu Glu Gln Leu Ile
            1100                1105                1110
Leu Glu Gly Asn Lys Ile Ser Gly Ile Cys Ser Pro Leu Arg Leu
            1115                1120                1125
Lys Glu Leu Lys Ile Leu Asn Leu Ser Lys Asn His Ile Ser Ser
            1130                1135                1140
Leu Ser Glu Asn Phe Leu Glu Ala Cys Pro Lys Val Glu Ser Phe
            1145                1150                1155
Ser Ala Arg Met Asn Phe Leu Ala Ala Met Pro Phe Leu Pro Pro
            1160                1165                1170
Ser Met Thr Ile Leu Lys Leu Ser Gln Asn Lys Phe Ser Cys Ile
            1175                1180                1185
Pro Glu Ala Ile Leu Asn Leu Pro His Leu Arg Ser Leu Asp Met
            1190                1195                1200
Ser Ser Asn Asp Ile Gln Tyr Leu Pro Gly Pro Ala His Trp Lys
            1205                1210                1215
Ser Leu Asn Leu Arg Glu Leu Leu Phe Ser His Asn Gln Ile Ser
            1220                1225                1230
Ile Leu Asp Leu Ser Glu Lys Ala Tyr Leu Trp Ser Arg Val Glu
            1235                1240                1245
Lys Leu His Leu Ser His Asn Lys Leu Lys Glu Ile Pro Pro Glu
            1250                1255                1260
Ile Gly Cys Leu Glu Asn Leu Thr Ser Leu Asp Val Ser Tyr Asn
            1265                1270                1275
Leu Glu Leu Arg Ser Phe Pro Asn Glu Met Gly Lys Leu Ser Lys
            1280                1285                1290
Ile Trp Asp Leu Pro Leu Asp Glu Leu His Leu Asn Phe Asp Phe
            1295                1300                1305
Lys His Ile Gly Cys Lys Ala Lys Asp Ile Ile Arg Phe Leu Gln
            1310                1315                1320
Gln Arg Leu Lys Lys Ala Val Pro Tyr Asn Arg Met Lys Leu Met
            1325                1330                1335
Ile Val Gly Asn Thr Gly Ser Gly Lys Thr Thr Leu Leu Gln Gln
            1340                1345                1350
Leu Met Lys Thr Lys Lys Ser Asp Leu Gly Met Gln Ser Ala Thr
            1355                1360                1365
```

-continued

```
Val Gly Ile Asp Val Lys Asp Trp Pro Ile Gln Ile Arg Asp Lys
    1370            1375            1380

Arg Lys Arg Asp Leu Val Leu Asn Val Trp Asp Phe Ala Gly Arg
    1385            1390            1395

Glu Glu Phe Tyr Ser Thr His Pro His Phe Met Thr Gln Arg Ala
    1400            1405            1410

Leu Tyr Leu Ala Val Tyr Asp Leu Ser Lys Gly Gln Ala Glu Val
    1415            1420            1425

Asp Ala Met Lys Pro Trp Leu Phe Asn Ile Lys Ala Arg Ala Ser
    1430            1435            1440

Ser Ser Pro Val Ile Leu Val Gly Thr His Leu Asp Val Ser Asp
    1445            1450            1455

Glu Lys Gln Arg Lys Ala Cys Met Ser Lys Ile Thr Lys Glu Leu
    1460            1465            1470

Leu Asn Lys Arg Gly Phe Pro Ala Ile Arg Asp Tyr His Phe Val
    1475            1480            1485

Asn Ala Thr Glu Glu Ser Asp Ala Leu Ala Lys Leu Arg Lys Thr
    1490            1495            1500

Ile Ile Asn Glu Ser Leu Asn Phe Lys Ile Arg Asp Gln Leu Val
    1505            1510            1515

Val Gly Gln Leu Ile Pro Asp Cys Tyr Val Glu Leu Glu Lys Ile
    1520            1525            1530

Ile Leu Ser Glu Arg Lys Asn Val Pro Ile Glu Phe Pro Val Ile
    1535            1540            1545

Asp Arg Lys Arg Leu Leu Gln Leu Val Arg Glu Asn Gln Leu Gln
    1550            1555            1560

Leu Asp Glu Asn Glu Leu Pro His Ala Val His Phe Leu Asn Glu
    1565            1570            1575

Ser Gly Val Leu Leu His Phe Gln Asp Pro Ala Leu Gln Leu Ser
    1580            1585            1590

Asp Leu Tyr Phe Val Glu Pro Lys Trp Leu Cys Lys Ile Met Ala
    1595            1600            1605

Gln Ile Leu Thr Val Lys Val Glu Gly Cys Pro Lys His Pro Lys
    1610            1615            1620

Gly Ile Ile Ser Arg Arg Asp Val Glu Lys Phe Leu Ser Lys Lys
    1625            1630            1635

Arg Lys Phe Pro Lys Asn Tyr Met Thr Gln Tyr Phe Lys Leu Leu
    1640            1645            1650

Glu Lys Phe Gln Ile Ala Leu Pro Ile Gly Glu Glu Tyr Leu Leu
    1655            1660            1665

Val Pro Ser Ser Leu Ser Asp His Arg Pro Val Ile Glu Leu Pro
    1670            1675            1680

His Cys Glu Asn Ser Glu Ile Ile Ile Arg Leu Tyr Glu Met Pro
    1685            1690            1695

Tyr Phe Pro Met Gly Phe Trp Ser Arg Leu Ile Asn Arg Leu Leu
    1700            1705            1710

Glu Ile Ser Pro Tyr Met Leu Ser Gly Arg Glu Arg Ala Leu Arg
    1715            1720            1725

Pro Asn Arg Met Tyr Trp Arg Gln Gly Ile Tyr Leu Asn Trp Ser
    1730            1735            1740

Pro Glu Ala Tyr Cys Leu Val Gly Ser Glu Val Leu Asp Asn His
    1745            1750            1755
```

```
Pro Glu Ser Phe Leu Lys Ile Thr Val Pro Ser Cys Arg Lys Gly
    1760            1765            1770

Cys Ile Leu Leu Gly Gln Val Val Asp His Ile Asp Ser Leu Met
    1775            1780            1785

Glu Glu Trp Phe Pro Gly Leu Leu Glu Ile Asp Ile Cys Gly Glu
    1790            1795            1800

Gly Glu Thr Leu Leu Lys Lys Trp Ala Leu Tyr Ser Phe Asn Asp
    1805            1810            1815

Gly Glu Glu His Gln Lys Ile Leu Leu Asp Asp Leu Met Lys Lys
    1820            1825            1830

Ala Glu Glu Gly Asp Leu Leu Val Asn Pro Asp Gln Pro Arg Leu
    1835            1840            1845

Thr Ile Pro Ile Ser Gln Ile Ala Pro Asp Leu Ile Leu Ala Asp
    1850            1855            1860

Leu Pro Arg Asn Ile Met Leu Asn Asn Asp Glu Leu Glu Phe Glu
    1865            1870            1875

Gln Ala Pro Glu Phe Leu Leu Gly Asp Gly Ser Phe Gly Ser Val
    1880            1885            1890

Tyr Arg Ala Ala Tyr Glu Gly Glu Glu Val Ala Val Lys Ile Phe
    1895            1900            1905

Asn Lys His Thr Ser Leu Arg Leu Leu Arg Gln Glu Leu Val Val
    1910            1915            1920

Leu Cys His Leu His His Pro Ser Leu Ile Ser Leu Leu Ala Ala
    1925            1930            1935

Gly Ile Arg Pro Arg Met Leu Val Met Glu Leu Ala Ser Lys Gly
    1940            1945            1950

Ser Leu Asp Arg Leu Leu Gln Gln Asp Lys Ala Ser Leu Thr Arg
    1955            1960            1965

Thr Leu Gln His Arg Ile Ala Leu His Val Ala Asp Gly Leu Arg
    1970            1975            1980

Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu Tyr Asp Ile Leu Thr Thr Gly Gly Arg Ile
    2060            2065            2070

Val Glu Gly Leu Lys Phe Pro Asn Glu Phe Asp Glu Leu Glu Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Lys Gln Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Val Cys Leu Thr Arg Arg Ile Leu Leu Pro Lys
    2135            2140            2145

Asn Val Ile Val Glu Cys Met Val Ala Thr His His Asn Ser Arg
```

```
                    2150                2155                2160

Asn Ala Ser Ile Trp Leu Gly Cys Gly His Thr Asp Arg Gly Gln
    2165                2170                2175

Leu Ser Phe Leu Asp Leu Asn Thr Glu Gly Tyr Thr Ser Glu Glu
    2180                2185                2190

Val Ala Asp Ser Arg Ile Leu Cys Leu Ala Leu Val His Leu Pro
    2195                2200                2205

Val Glu Lys Glu Ser Trp Ile Val Ser Gly Thr Gln Ser Gly Thr
    2210                2215                2220

Leu Leu Val Ile Asn Thr Glu Asp Gly Lys Lys Arg His Thr Leu
    2225                2230                2235

Glu Lys Met Thr Asp Ser Val Thr Cys Leu Tyr Cys Asn Ser Phe
    2240                2245                2250

Ser Lys Gln Ser Lys Gln Lys Asn Phe Leu Leu Val Gly Thr Ala
    2255                2260                2265

Asp Gly Lys Leu Ala Ile Phe Glu Asp Lys Thr Val Lys Leu Lys
    2270                2275                2280

Gly Ala Ala Pro Leu Lys Ile Leu Asn Ile Gly Asn Val Ser Thr
    2285                2290                2295

Pro Leu Met Cys Leu Ser Glu Ser Thr Asn Ser Thr Glu Arg Asn
    2300                2305                2310

Val Met Trp Gly Gly Cys Gly Thr Lys Ile Phe Ser Phe Ser Asn
    2315                2320                2325

Asp Phe Thr Ile Gln Lys Leu Ile Glu Thr Arg Thr Ser Gln Leu
    2330                2335                2340

Phe Ser Tyr Ala Ala Phe Ser Asp Ser Asn Ile Ile Thr Val Val
    2345                2350                2355

Val Asp Thr Ala Leu Tyr Ile Ala Lys Gln Asn Ser Pro Val Val
    2360                2365                2370

Glu Val Trp Asp Lys Lys Thr Glu Lys Leu Cys Arg Leu Ile Asp
    2375                2380                2385

Cys Val His Phe Leu Arg Glu Val Thr Val Lys Glu Asn Lys Glu
    2390                2395                2400

Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly Gly His
    2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
    2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
    2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
    2510                2515                2520

Thr Ser Val Glu
    2525

<210> SEQ ID NO 58
```

<211> LENGTH: 2527
<212> TYPE: PRT
<213> ORGANISM: Homo sapiens

<400> SEQUENCE: 58

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
    370                 375                 380

His Glu Lys Ile Gly Asp Glu Asp Gly His Phe Pro Ala His Arg Glu
```

```
            385                 390                 395                 400
Val Met Leu Ser Met Leu Met His Ser Ser Lys Glu Val Phe Gln
                    405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
                435                 440                 445

Met Gln Lys His Ile His Ser Pro Glu Val Ala Glu Ser Gly Cys Lys
            450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                    485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
                515                 520                 525

Lys Leu Asn Met Val Lys Lys Gln Cys Phe Lys Asn Asp Ile His Lys
            530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                    565                 570                 575

Leu Glu Met Leu Ser Leu Glu Gly Ala Met Asp Ser Val Leu His Thr
                580                 585                 590

Leu Gln Met Tyr Pro Asp Asp Gln Glu Ile Gln Cys Leu Gly Leu Ser
                595                 600                 605

Leu Ile Gly Tyr Leu Ile Thr Lys Lys Asn Val Phe Ile Gly Thr Gly
            610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                    645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
                675                 680                 685

Gln Gln Phe Leu Asn Leu Cys Cys Lys Cys Phe Ala Lys Val Ala Met
            690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                    725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Leu Asn Ser Gly Ser Arg Glu
            755                 760                 765

Gln Asp Val Arg Lys Ala Leu Thr Ile Ser Ile Gly Lys Gly Asp Ser
            770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                    805                 810                 815
```

```
Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
            850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
            930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
            995                 1000                 1005

His Leu  Glu His Leu  Glu Lys  Leu Glu Leu His Gln  Asn Ala Leu
    1010                1015                1020

Thr Ser  Phe Pro Gln Gln  Leu  Cys Glu Thr Leu  Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
    1175                1180                1185

Pro Glu  Ala Ile Leu Asn Leu  Pro His Leu Arg Ser  Leu Asp Met
    1190                1195                1200

Ser Ser  Asn Asp Ile Gln Tyr  Leu Pro Gly Pro Ala  His Trp Lys
    1205                1210                1215
```

-continued

| | | | | | | | | | | | |
|---|---|---|---|---|---|---|---|---|---|---|---|
| Ser | Leu | Asn | Leu | Arg | Glu | Leu | Leu | Phe | Ser | His | Asn | Gln | Ile | Ser |

Ser Leu Asn Leu Arg Glu Leu Leu Phe Ser His Asn Gln Ile Ser
    1220            1225            1230

Ile Leu Asp Leu Ser Glu Lys Ala Tyr Leu Trp Ser Arg Val Glu
    1235            1240            1245

Lys Leu His Leu Ser His Asn Lys Leu Lys Glu Ile Pro Pro Glu
    1250            1255            1260

Ile Gly Cys Leu Glu Asn Leu Thr Ser Leu Asp Val Ser Tyr Asn
    1265            1270            1275

Leu Glu Leu Arg Ser Phe Pro Asn Glu Met Gly Lys Leu Ser Lys
    1280            1285            1290

Ile Trp Asp Leu Pro Leu Asp Glu Leu His Leu Asn Phe Asp Phe
    1295            1300            1305

Lys His Ile Gly Cys Lys Ala Lys Asp Ile Ile Arg Phe Leu Gln
    1310            1315            1320

Gln Arg Leu Lys Lys Ala Val Pro Tyr Asn Arg Met Lys Leu Met
    1325            1330            1335

Ile Val Gly Asn Thr Gly Ser Gly Lys Thr Thr Leu Leu Gln Gln
    1340            1345            1350

Leu Met Lys Thr Lys Lys Ser Asp Leu Gly Met Gln Ser Ala Thr
    1355            1360            1365

Val Gly Ile Asp Val Lys Asp Trp Pro Ile Gln Ile Arg Asp Lys
    1370            1375            1380

Arg Lys Arg Asp Leu Val Leu Asn Val Trp Asp Phe Ala Gly Arg
    1385            1390            1395

Glu Glu Phe Tyr Ser Thr His Pro His Phe Met Thr Gln Arg Ala
    1400            1405            1410

Leu Tyr Leu Ala Val Tyr Asp Leu Ser Lys Gly Gln Ala Glu Val
    1415            1420            1425

Asp Ala Met Lys Pro Trp Leu Phe Asn Ile Lys Ala Cys Ala Ser
    1430            1435            1440

Ser Ser Pro Val Ile Leu Val Gly Thr His Leu Asp Val Ser Asp
    1445            1450            1455

Glu Lys Gln Arg Lys Ala Cys Met Ser Lys Ile Thr Lys Glu Leu
    1460            1465            1470

Leu Asn Lys Arg Gly Phe Pro Ala Ile Arg Asp Tyr His Phe Val
    1475            1480            1485

Asn Ala Thr Glu Glu Ser Asp Ala Leu Ala Lys Leu Arg Lys Thr
    1490            1495            1500

Ile Ile Asn Glu Ser Leu Asn Phe Lys Ile Arg Asp Gln Leu Val
    1505            1510            1515

Val Gly Gln Leu Ile Pro Asp Cys Tyr Val Glu Leu Glu Lys Ile
    1520            1525            1530

Ile Leu Ser Glu Arg Lys Asn Val Pro Ile Glu Phe Pro Val Ile
    1535            1540            1545

Asp Arg Lys Arg Leu Leu Gln Leu Val Arg Glu Asn Gln Leu Gln
    1550            1555            1560

Leu Asp Glu Asn Glu Leu Pro His Ala Val His Phe Leu Asn Glu
    1565            1570            1575

Ser Gly Val Leu Leu His Phe Gln Asp Pro Ala Leu Gln Leu Ser
    1580            1585            1590

Asp Leu Tyr Phe Val Glu Pro Lys Trp Leu Cys Lys Ile Met Ala
    1595            1600            1605

Gln Ile Leu Thr Val Lys Val Glu Gly Cys Pro Lys His Pro Lys

```
            1610                1615                1620
Gly Ile Ile Ser Arg Arg Asp Val Glu Lys Phe Leu Ser Lys Lys
        1625                1630                1635
Arg Lys Phe Pro Lys Asn Tyr Met Thr Gln Tyr Phe Lys Leu Leu
        1640                1645                1650
Glu Lys Phe Gln Ile Ala Leu Pro Ile Gly Glu Glu Tyr Leu Leu
        1655                1660                1665
Val Pro Ser Ser Leu Ser Asp His Arg Pro Val Ile Glu Leu Pro
        1670                1675                1680
His Cys Glu Asn Ser Glu Ile Ile Ile Arg Leu Tyr Glu Met Pro
        1685                1690                1695
Tyr Phe Pro Met Gly Phe Trp Ser Arg Leu Ile Asn Arg Leu Leu
        1700                1705                1710
Glu Ile Ser Pro Tyr Met Leu Ser Gly Arg Glu Arg Ala Leu Arg
        1715                1720                1725
Pro Asn Arg Met Tyr Trp Arg Gln Gly Ile Tyr Leu Asn Trp Ser
        1730                1735                1740
Pro Glu Ala Tyr Cys Leu Val Gly Ser Glu Val Leu Asp Asn His
        1745                1750                1755
Pro Glu Ser Phe Leu Lys Ile Thr Val Pro Ser Cys Arg Lys Gly
        1760                1765                1770
Cys Ile Leu Leu Gly Gln Val Val Asp His Ile Asp Ser Leu Met
        1775                1780                1785
Glu Glu Trp Phe Pro Gly Leu Leu Glu Ile Asp Ile Cys Gly Glu
        1790                1795                1800
Gly Glu Thr Leu Leu Lys Lys Trp Ala Leu Tyr Ser Phe Asn Asp
        1805                1810                1815
Gly Glu Glu His Gln Lys Ile Leu Leu Asp Asp Leu Met Lys Lys
        1820                1825                1830
Ala Glu Glu Gly Asp Leu Leu Val Asn Pro Asp Gln Pro Arg Leu
        1835                1840                1845
Thr Ile Pro Ile Ser Gln Ile Ala Pro Asp Leu Ile Leu Ala Asp
        1850                1855                1860
Leu Pro Arg Asn Ile Met Leu Asn Asn Asp Glu Leu Glu Phe Glu
        1865                1870                1875
Gln Ala Pro Glu Phe Leu Leu Gly Asp Gly Ser Phe Gly Ser Val
        1880                1885                1890
Tyr Arg Ala Ala Tyr Glu Gly Glu Glu Val Ala Val Lys Ile Phe
        1895                1900                1905
Asn Lys His Thr Ser Leu Arg Leu Leu Arg Gln Glu Leu Val Val
        1910                1915                1920
Leu Cys His Leu His His Pro Ser Leu Ile Ser Leu Leu Ala Ala
        1925                1930                1935
Gly Ile Arg Pro Arg Met Leu Val Met Glu Leu Ala Ser Lys Gly
        1940                1945                1950
Ser Leu Asp Arg Leu Leu Gln Gln Asp Lys Ala Ser Leu Thr Arg
        1955                1960                1965
Thr Leu Gln His Arg Ile Ala Leu His Val Ala Asp Gly Leu Arg
        1970                1975                1980
Tyr Leu His Ser Ala Met Ile Ile Tyr Arg Asp Leu Lys Pro His
        1985                1990                1995
Asn Val Leu Leu Phe Thr Leu Tyr Pro Asn Ala Ala Ile Ile Ala
        2000                2005                2010
```

```
Lys Ile Ala Asp Tyr Gly Ile Ala Gln Tyr Cys Cys Arg Met Gly
2015                 2020                 2025

Ile Lys Thr Ser Glu Gly Thr Pro Gly Phe Arg Ala Pro Glu Val
    2030                 2035                 2040

Ala Arg Gly Asn Val Ile Tyr Asn Gln Gln Ala Asp Val Tyr Ser
    2045                 2050                 2055

Phe Gly Leu Leu Leu Tyr Asp Ile Leu Thr Thr Gly Gly Arg Ile
    2060                 2065                 2070

Val Glu Gly Leu Lys Phe Pro Asn Glu Phe Asp Glu Leu Glu Ile
    2075                 2080                 2085

Gln Gly Lys Leu Pro Asp Pro Val Lys Glu Tyr Gly Cys Ala Pro
    2090                 2095                 2100

Trp Pro Met Val Glu Lys Leu Ile Lys Gln Cys Leu Lys Glu Asn
    2105                 2110                 2115

Pro Gln Glu Arg Pro Thr Ser Ala Gln Val Phe Asp Ile Leu Asn
    2120                 2125                 2130

Ser Ala Glu Leu Val Cys Leu Thr Arg Arg Ile Leu Leu Pro Lys
    2135                 2140                 2145

Asn Val Ile Val Glu Cys Met Val Ala Thr His His Asn Ser Arg
    2150                 2155                 2160

Asn Ala Ser Ile Trp Leu Gly Cys Gly His Thr Asp Arg Gly Gln
    2165                 2170                 2175

Leu Ser Phe Leu Asp Leu Asn Thr Glu Gly Tyr Thr Ser Glu Glu
    2180                 2185                 2190

Val Ala Asp Ser Arg Ile Leu Cys Leu Ala Leu Val His Leu Pro
    2195                 2200                 2205

Val Glu Lys Glu Ser Trp Ile Val Ser Gly Thr Gln Ser Gly Thr
    2210                 2215                 2220

Leu Leu Val Ile Asn Thr Glu Asp Gly Lys Lys Arg His Thr Leu
    2225                 2230                 2235

Glu Lys Met Thr Asp Ser Val Thr Cys Leu Tyr Cys Asn Ser Phe
    2240                 2245                 2250

Ser Lys Gln Ser Lys Gln Lys Asn Phe Leu Leu Val Gly Thr Ala
    2255                 2260                 2265

Asp Gly Lys Leu Ala Ile Phe Glu Asp Lys Thr Val Lys Leu Lys
    2270                 2275                 2280

Gly Ala Ala Pro Leu Lys Ile Leu Asn Ile Gly Asn Val Ser Thr
    2285                 2290                 2295

Pro Leu Met Cys Leu Ser Glu Ser Thr Asn Ser Thr Glu Arg Asn
    2300                 2305                 2310

Val Met Trp Gly Gly Cys Gly Thr Lys Ile Phe Ser Phe Ser Asn
    2315                 2320                 2325

Asp Phe Thr Ile Gln Lys Leu Ile Glu Thr Arg Thr Ser Gln Leu
    2330                 2335                 2340

Phe Ser Tyr Ala Ala Phe Ser Asp Ser Asn Ile Ile Thr Val Val
    2345                 2350                 2355

Val Asp Thr Ala Leu Tyr Ile Ala Lys Gln Asn Ser Pro Val Val
    2360                 2365                 2370

Glu Val Trp Asp Lys Lys Thr Glu Lys Leu Cys Gly Leu Ile Asp
    2375                 2380                 2385

Cys Val His Phe Leu Arg Glu Val Thr Val Lys Glu Asn Lys Glu
    2390                 2395                 2400
```

```
Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly His
    2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
    2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
    2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
    2510                2515                2520

Thr Ser Val Glu
    2525

<210> SEQ ID NO 59
<211> LENGTH: 2527
<212> TYPE: PRT
<213> ORGANISM: Homo sapiens

<400> SEQUENCE: 59

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
                20                  25                  30

Glu Thr Leu Val Gln Ile Leu Glu Asp Leu Leu Val Phe Thr Tyr Ser
            35                  40                  45

Glu His Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
    210                 215                 220

Val Leu His Cys Leu His Ser Leu Ala Ile Pro Cys Asn Asn Val Glu
225                 230                 235                 240
```

```
Val Leu Met Ser Gly Asn Val Arg Cys Tyr Asn Ile Val Val Glu Ala
            245                 250                 255
Met Lys Ala Phe Pro Met Ser Glu Arg Ile Gln Glu Val Ser Cys Cys
            260                 265                 270
Leu Leu His Arg Leu Thr Leu Gly Asn Phe Phe Asn Ile Leu Val Leu
            275                 280                 285
Asn Glu Val His Glu Phe Val Val Lys Ala Val Gln Gln Tyr Pro Glu
            290                 295                 300
Asn Ala Ala Leu Gln Ile Ser Ala Leu Ser Cys Leu Ala Leu Leu Thr
305                 310                 315                 320
Glu Thr Ile Phe Leu Asn Gln Asp Leu Glu Glu Lys Asn Glu Asn Gln
            325                 330                 335
Glu Asn Asp Asp Glu Gly Glu Glu Asp Lys Leu Phe Trp Leu Glu Ala
            340                 345                 350
Cys Tyr Lys Ala Leu Thr Trp His Arg Lys Asn Lys His Val Gln Glu
            355                 360                 365
Ala Ala Cys Trp Ala Leu Asn Asn Leu Leu Met Tyr Gln Asn Ser Leu
            370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
            405                 410                 415
Ala Ser Ala Asn Ala Leu Ser Thr Leu Leu Glu Gln Asn Val Asn Phe
            420                 425                 430
Arg Lys Ile Leu Leu Ser Lys Gly Ile His Leu Asn Val Leu Glu Leu
            435                 440                 445
Met Gln Lys His Ile His Ser Pro Glu Val Ala Glu Ser Gly Cys Lys
            450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
            485                 490                 495
Ser Leu Pro Val Gln Leu Glu Ala Leu Arg Ala Ile Leu His Phe Ile
            500                 505                 510
Val Pro Gly Met Pro Glu Glu Ser Arg Glu Asp Thr Glu Phe His His
            515                 520                 525
Lys Leu Asn Met Val Lys Lys Gln Cys Phe Lys Asn Asp Ile His Lys
            530                 535                 540
Leu Val Leu Ala Ala Leu Asn Arg Phe Ile Gly Asn Pro Gly Ile Gln
545                 550                 555                 560
Lys Cys Gly Leu Lys Val Ile Ser Ser Ile Val His Phe Pro Asp Ala
            565                 570                 575
Leu Glu Met Leu Ser Leu Glu Gly Ala Met Asp Ser Val Leu His Thr
            580                 585                 590
Leu Gln Met Tyr Pro Asp Asp Gln Glu Ile Gln Cys Leu Gly Leu Ser
            595                 600                 605
Leu Ile Gly Tyr Leu Ile Thr Lys Lys Asn Val Phe Ile Gly Thr Gly
            610                 615                 620
His Leu Leu Ala Lys Ile Leu Val Ser Ser Leu Tyr Arg Phe Lys Asp
625                 630                 635                 640
Val Ala Glu Ile Gln Thr Lys Gly Phe Gln Thr Ile Leu Ala Ile Leu
            645                 650                 655
```

-continued

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
            690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
            725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
            755                 760                 765

Gln Asp Val Arg Lys Ala Leu Thr Ile Ser Ile Gly Lys Gly Asp Ser
            770                 775                 780

Gln Ile Ile Ser Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
            805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
            885                 890                 895

Gly Ser Glu Gly Ser Phe Leu Val Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
            930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
            995                 1000                1005

His Leu Glu His Leu Glu Lys Leu Glu Leu His Gln Asn Ala Leu
            1010                1015                1020

Thr Ser Phe Pro Gln Gln Leu Cys Glu Thr Leu Lys Ser Leu Thr
            1025                1030                1035

His Leu Asp Leu His Ser Asn Lys Phe Thr Ser Phe Pro Ser Tyr
            1040                1045                1050

Leu Leu Lys Met Ser Cys Ile Ala Asn Leu Asp Val Ser Arg Asn
            1055                1060                1065

Asp Ile Gly Pro Ser Val Val Leu Asp Pro Thr Val Lys Cys Pro

```
                1070                1075                1080
Thr Leu Lys Gln Phe Asn Leu Ser Tyr Asn Gln Leu Ser Phe Val
    1085                1090                1095

Pro Glu Asn Leu Thr Asp Val Val Glu Lys Leu Glu Gln Leu Ile
    1100                1105                1110

Leu Glu Gly Asn Lys Ile Ser Gly Ile Cys Ser Pro Leu Arg Leu
    1115                1120                1125

Lys Glu Leu Lys Ile Leu Asn Leu Ser Lys Asn His Ile Ser Ser
    1130                1135                1140

Leu Ser Glu Asn Phe Leu Glu Ala Cys Pro Lys Val Glu Ser Phe
    1145                1150                1155

Ser Ala Arg Met Asn Phe Leu Ala Ala Met Pro Phe Leu Pro Pro
    1160                1165                1170

Ser Met Thr Ile Leu Lys Leu Ser Gln Asn Lys Phe Ser Cys Ile
    1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
    1280                1285                1290

Ile Trp Asp Leu Pro Leu Asp Glu Leu His Leu Asn Phe Asp Phe
    1295                1300                1305

Lys His Ile Gly Cys Lys Ala Lys Asp Ile Ile Arg Phe Leu Gln
    1310                1315                1320

Gln Arg Leu Lys Lys Ala Val Pro Tyr Asn Arg Met Lys Leu Met
    1325                1330                1335

Ile Val Gly Asn Thr Gly Ser Gly Lys Thr Thr Leu Leu Gln Gln
    1340                1345                1350

Leu Met Lys Thr Lys Lys Ser Asp Leu Gly Met Gln Ser Ala Thr
    1355                1360                1365

Val Gly Ile Asp Val Lys Asp Trp Pro Ile Gln Ile Arg Asp Lys
    1370                1375                1380

Arg Lys Arg Asp Leu Val Leu Asn Val Trp Asp Phe Ala Gly Arg
    1385                1390                1395

Glu Glu Phe Tyr Ser Thr His Pro His Phe Met Thr Gln Arg Ala
    1400                1405                1410

Leu Tyr Leu Ala Val Tyr Asp Leu Ser Lys Gly Gln Ala Glu Val
    1415                1420                1425

Asp Ala Met Lys Pro Trp Leu Phe Asn Ile Lys Ala Arg Ala Ser
    1430                1435                1440

Ser Ser Pro Val Ile Leu Val Gly Thr His Leu Asp Val Ser Asp
    1445                1450                1455

Glu Lys Gln Arg Lys Ala Cys Met Ser Lys Ile Thr Lys Glu Leu
    1460                1465                1470
```

-continued

```
Leu Asn Lys Arg Gly Phe Pro Ala Ile Arg Asp Tyr His Phe Val
    1475            1480            1485

Asn Ala Thr Glu Glu Ser Asp Ala Leu Ala Lys Leu Arg Lys Thr
    1490            1495            1500

Ile Ile Asn Glu Ser Leu Asn Phe Lys Ile Arg Asp Gln Leu Val
    1505            1510            1515

Val Gly Gln Leu Ile Pro Asp Cys Tyr Val Glu Leu Glu Lys Ile
    1520            1525            1530

Ile Leu Ser Glu Arg Lys Asn Val Pro Ile Glu Phe Pro Val Ile
    1535            1540            1545

Asp Arg Lys Arg Leu Leu Gln Leu Val Arg Glu Asn Gln Leu Gln
    1550            1555            1560

Leu Asp Glu Asn Glu Leu Pro His Ala Val His Phe Leu Asn Glu
    1565            1570            1575

Ser Gly Val Leu Leu His Phe Gln Asp Pro Ala Leu Gln Leu Ser
    1580            1585            1590

Asp Leu Tyr Phe Val Glu Pro Lys Trp Leu Cys Lys Ile Met Ala
    1595            1600            1605

Gln Ile Leu Thr Val Lys Val Glu Gly Cys Pro Lys His Pro Lys
    1610            1615            1620

Gly Ile Ile Ser Pro Arg Asp Val Glu Lys Phe Leu Ser Lys Lys
    1625            1630            1635

Arg Lys Phe Pro Lys Asn Tyr Met Thr Gln Tyr Phe Lys Leu Leu
    1640            1645            1650

Glu Lys Phe Gln Ile Ala Leu Pro Ile Gly Glu Glu Tyr Leu Leu
    1655            1660            1665

Val Pro Ser Ser Leu Ser Asp His Arg Pro Val Ile Glu Leu Pro
    1670            1675            1680

His Cys Glu Asn Ser Glu Ile Ile Ile Arg Leu Tyr Glu Met Pro
    1685            1690            1695

Tyr Phe Pro Met Gly Phe Trp Ser Arg Leu Ile Asn Arg Leu Leu
    1700            1705            1710

Glu Ile Ser Pro Tyr Met Leu Ser Gly Arg Glu Arg Ala Leu Arg
    1715            1720            1725

Pro Asn Arg Met Tyr Trp Arg Gln Gly Ile Tyr Leu Asn Trp Ser
    1730            1735            1740

Pro Glu Ala Tyr Cys Leu Val Gly Ser Glu Val Leu Asp Asn His
    1745            1750            1755

Pro Glu Ser Phe Leu Lys Ile Thr Val Pro Ser Cys Arg Lys Gly
    1760            1765            1770

Cys Ile Leu Leu Gly Gln Val Val Asp His Ile Asp Ser Leu Met
    1775            1780            1785

Glu Glu Trp Phe Pro Gly Leu Leu Glu Ile Asp Ile Cys Gly Glu
    1790            1795            1800

Gly Glu Thr Leu Leu Lys Lys Trp Ala Leu Tyr Ser Phe Asn Asp
    1805            1810            1815

Gly Glu Glu His Gln Lys Ile Leu Leu Asp Asp Leu Met Lys Lys
    1820            1825            1830

Ala Glu Glu Gly Asp Leu Leu Val Asn Pro Asp Gln Pro Arg Leu
    1835            1840            1845

Thr Ile Pro Ile Ser Gln Ile Ala Pro Asp Leu Ile Leu Ala Asp
    1850            1855            1860
```

```
Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980

Tyr Leu His Ser Ala Met Ile Ile Tyr Arg Asp Leu Lys Pro His
    1985                1990                1995

Asn Val Leu Leu Phe Thr Leu Tyr Pro Asn Ala Ala Ile Ile Ala
    2000                2005                2010

Lys Ile Ala Asp Tyr Gly Ile Ala Gln Tyr Cys Cys Arg Met Gly
    2015                2020                2025

Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070

Val Glu Gly Leu Lys Phe Pro Asn Glu Phe Asp Glu Leu Glu Ile
    2075                2080                2085

Gln Gly Lys Leu Pro Asp Pro Val Lys Glu Tyr Gly Cys Ala Pro
    2090                2095                2100

Trp Pro Met Val Glu Lys Leu Ile Lys Gln Cys Leu Lys Glu Asn
    2105                2110                2115

Pro Gln Glu Arg Pro Thr Ser Ala Gln Val Phe Asp Ile Leu Asn
    2120                2125                2130

Ser Ala Glu Leu Val Cys Leu Thr Arg Arg Ile Leu Leu Pro Lys
    2135                2140                2145

Asn Val Ile Val Glu Cys Met Val Ala Thr His His Asn Ser Arg
    2150                2155                2160

Asn Ala Ser Ile Trp Leu Gly Cys Gly His Thr Asp Arg Gly Gln
    2165                2170                2175

Leu Ser Phe Leu Asp Leu Asn Thr Glu Gly Tyr Thr Ser Glu Glu
    2180                2185                2190

Val Ala Asp Ser Arg Ile Leu Cys Leu Ala Leu Val His Leu Pro
    2195                2200                2205

Val Glu Lys Glu Ser Trp Ile Val Ser Gly Thr Gln Ser Gly Thr
    2210                2215                2220

Leu Leu Val Ile Asn Thr Glu Asp Gly Lys Lys Arg His Thr Leu
    2225                2230                2235

Glu Lys Met Thr Asp Ser Val Thr Cys Leu Tyr Cys Asn Ser Phe
    2240                2245                2250

Ser Lys Gln Ser Lys Gln Lys Asn Phe Leu Leu Val Gly Thr Ala
```

-continued

```
                2255                    2260                    2265
    Asp Gly Lys Leu Ala Ile Phe Glu Asp Lys Thr Val Lys Leu Lys
            2270                    2275                    2280

Gly Ala Ala Pro Leu Lys Ile Leu Asn Ile Gly Asn Val Ser Thr
            2285                    2290                    2295

Pro Leu Met Cys Leu Ser Glu Ser Thr Asn Ser Thr Glu Arg Asn
            2300                    2305                    2310

Val Met Trp Gly Gly Cys Gly Thr Lys Ile Phe Ser Phe Ser Asn
            2315                    2320                    2325

Asp Phe Thr Ile Gln Lys Leu Ile Glu Thr Arg Thr Ser Gln Leu
            2330                    2335                    2340

Phe Ser Tyr Ala Ala Phe Ser Asp Ser Asn Ile Ile Thr Val Val
            2345                    2350                    2355

Val Asp Thr Ala Leu Tyr Ile Ala Lys Gln Asn Ser Pro Val Val
            2360                    2365                    2370

Glu Val Trp Asp Lys Lys Thr Glu Lys Leu Cys Gly Leu Ile Asp
            2375                    2380                    2385

Cys Val His Phe Leu Arg Glu Val Thr Val Lys Glu Asn Lys Glu
            2390                    2395                    2400

Ser Lys His Lys Met Ser Tyr Ser Gly Arg Val Lys Thr Leu Cys
            2405                    2410                    2415

Leu Gln Lys Asn Thr Ala Leu Trp Ile Gly Thr Gly Gly Gly His
            2420                    2425                    2430

Ile Leu Leu Leu Asp Leu Ser Thr Arg Arg Leu Ile Arg Val Ile
            2435                    2440                    2445

Tyr Asn Phe Cys Asn Ser Val Arg Val Met Met Thr Ala Gln Leu
            2450                    2455                    2460

Gly Ser Leu Lys Asn Val Met Leu Val Leu Gly Tyr Asn Arg Lys
            2465                    2470                    2475

Asn Thr Glu Gly Thr Gln Lys Gln Lys Glu Ile Gln Ser Cys Leu
            2480                    2485                    2490

Thr Val Trp Asp Ile Asn Leu Pro His Glu Val Gln Asn Leu Glu
            2495                    2500                    2505

Lys His Ile Glu Val Arg Lys Glu Leu Ala Glu Lys Met Arg Arg
            2510                    2515                    2520

Thr Ser Val Glu
            2525
```

METHODS AND COMPOSITIONS FOR GENE CORRECTION

CROSS-REFERENCE TO RELATED APPLICATIONS

The present application claims the benefit of U.S. Provisional Application Nos. 61/460,686, filed Jan. 5, 2011 and 61/517,478, filed Apr. 20, 2011, the disclosures of which are hereby incorporated by reference in their entireties.

TECHNICAL FIELD

The present disclosure is in the fields of genome editing.

BACKGROUND

Parkinson's disease (PD) is a neurodegenerative disease that afflicts approximately 4-6 million people worldwide. In the United States, approximately one to two hundred people per 100,000 have PD. Interestingly, the prevalence among Amish people is approximately 970 per 100,000 although the basis for this high rate, be it genetic or environmental, is not known. The prevalence of PD increases in the older population, with approximately 4% of people over the age of 80 suffering from this disease (Davie (2008) *Brit Med Bull* 86(1) p. 109), although 10% of patients are under 40 years of age (Kumari (2009) *FEBS J* 276(22) p. 6455).

Typically a patient diagnosed with PD is identified by several hallmark physical behaviors: bradykinesia, rigidity and rest tremor. Often these physical symptoms are asymmetric. Within the brain, PD is characterized by a progressive and profound loss of neuromelanin-containing dopaminergic neurons in the substantia nigra pars compacta with the presence of eosinophillic, intracytoplasmic and proteinaceous inclusions termed Lewy bodies in the surviving neurons (Davie, ibid and Kumari, ibid). By the time of death, this region will have lost 50-70% of its neurons as compared to an individual without PD.

Lewy bodies are α-synuclein reactive inclusions that are made up of made of several neurofilament proteins combined with proteolytic enzymes. Lewy bodies are found in PD, and a variant of dementia called Dementia with Lewy Bodies, but are not observed in any other neurological diseases.

It appears to have many factors can play a role in disease onset and/or progression of PD. In particular, genes including α-synuclein (PARK1/PARK4, SCNA), parkin (PARK 2), PARK 3, ubiquitin carboxy-terminal hydrolase L1 (PARK5) etc.) and environmental factors such as exposure to heavy metals and certain pesticides are believed to contribute to PD.

Additionally, genetic mutations in the leucine rich repeat kinase 2 gene (LRRK2, also known as PARK8) has been identified to be involved in both familial and sporatic forms of PD. In fact, studies suggest that LRRK2 mutations may be responsible for between 5 and 13% of familial PD, and from 1 to 5% of sporadic PD. The protein itself is a large (>280 kD) multidomain protein containing the following known domains: armadillo (ARM), ankryn (ANK), LRR, Ras of complex proteins (ROC), C-terminal of ROC (COR), mitogen-activated protein kinase kinase kinase and WD40. Thus, LRRK2 contains several protein-protein interactive domains (ARM/ANK, LRR and WD40) suggesting that LRRK2 plays a role in protein complex formation (Kumari, ibid). Several clusters of mutations have been identified which fall across its length of the gene, with the majority of pathological mutations clustering in the enzymatic domains of the protein.

Specifically, the LRRK2 mutation G2019S has been suggested to play an important role in PD in some ethnicities. Although prevalence among Asians, South Africans and some Europeans (of Polish, Greek and German descent) is quite low, among Ashkenazi Jews and North African Arabs, the prevalence is from 37-40%. In the US and the rest of Europe, G2019S accounts for approximately 1-7% of familial PD and 1-3% of sporadic PD in Caucasians (Kumari, ibid). The mutation is autosomal dominant and the lifetime penetrance for the mutation has been estimated at 31.8%. The SNP responsible for this missense mutation in patients is annotated as rs34637584 in the human genome, and is a G to A substitution at the genomic level (6055G>A). The G2019S mutation has been shown to increase LRRK2 kinase activity, and is found in the within the activation domain of the protein (Luzon-Toro, (2007) *Hum Mol Genet* 16(17) p. 2031).

The α-synuclein protein is an 140 amino acid protein comprising three domains: an N-terminal amphipathic domain comprising repeats of KTKEGV (SEQ ID NO: 51), a central hydrophobic, non-amyloid domain, and an acidic C-terminal domain. Increased gene dosage of α-synuclein has been shown to be in and of itself, a toxic event that leads to PD. Gene duplications of α-synuclein, which lead to increased gene expression, causes rare cases Of autosomal dominant PD. The function of the α-synuclein gene (SNCA) in a wild type setting is still unclear, but it appears that it plays a role in the regulation of autophagy (Winslow and Rubensztein (2010, online publication) Autophagy 7:4, p 1-3). It appears that overexpression of the protein inhibits the secretory pathway by a loss of function of the Rabla protein which is involved in autophagasome formation at a very early stage of the autophagy process. This in turn may lead to the cellular pathologies observed in PD: abnormal protein aggregation, mitochondrial abnormalities, increased levels of reactive oxygen species and increased sensitivity to cell death (Winslow and Rubensztein ibid).

In addition to increased gene dosage of the wild type SCNA gene, three mutations have been found which are also associated with PD. The three mutations, A53T, A30P, and E46K are all localized in the N-terminal domain of the protein, and appear to exacerbate toxic fibril formation (Perkevi et al (2009) *The Anatomical Record* 292 (12): 1893). However, cellular and transgenic animal models expressing such mutants only partially recapitulate PD pathology. See, Dawson et al. (2010) Neuron 66(5):646-61. Individuals with PD caused by α-synuclein mutation have similar clinical and pathological features of their PD as patients with idiopathic PD, however the onset of symptoms occurs significantly than typically seen with other PD patients (Pankratz and Foroud (2004) *Am Soc Exp Neu Ther* 1:235-242).

Thus, there remains a need for the development of novel anti-PD strategies to model and treat PD based on investigation of LRRK2 and SCNA mutations.

SUMMARY

Disclosed herein are methods and compositions for generating models for studying the function of PD-related genes, models for PD drug discovery and for treating PD. In particular, methods and compositions for altering PD related genetic loci such as SCNA and LRRK2 are described. The compositions and methods described herein can be used for genome editing, including, but not limited to: cleaving of one or more genes in an animal cell resulting in targeted alteration (insertion, deletion and/or substitution mutations) in one or more genes, including the incorporation of these targeted alterations into the germline; targeted introduction of non-endogenous nucleic acid sequences, the partial or complete inactivation of one or more genes in an animal; methods of inducing homology-directed repair; and generation of transgenic animals (e.g., rodents and non-human primates).

In one aspect, described herein is a zinc-finger protein (ZFP) that binds to target site in a LRRK2 or SCNA gene in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a LRRK2 or SCNA gene.

The ZFN may bind to and/or cleave a LRRK2 or SCNA gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein is a TALE protein (Transcription activator like) that binds to target site in a LRRK2 or SCNA gene in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the TALE DNA binding domain recognizes a target site in a LRRK2 or SCNA gene.

The TALEN may bind to and/or cleave a LRRK2 or SCNA gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein are compositions comprising one or more of the zinc-finger or TALE nucleases described herein. In certain embodiments, the composition comprises one or more zinc-finger or TALE nucleases in combination with a pharmaceutically acceptable excipient.

In another aspect, described herein is a polynucleotide encoding one or more ZFNs or TALENs described herein. The polynucleotide may be, for example, mRNA.

In another aspect, described herein is a ZFN or TALEN expression vector comprising a polynucleotide, encoding one or more ZFNs or TALENs described herein, operably linked to a promoter.

In another aspect, described herein is a host cell comprising one or more ZFN or TALEN expression vectors. The host cell may be stably transformed or transiently transfected or a combination thereof with one or more ZFP or TALEN expression vectors. In one embodiment, the host cell is an embryonic stem cell. In other embodiments, the one or more ZFP or TALEN expression vectors express one or more ZFNs or TALENs in the host cell. In another embodiment, the host cell may further comprise an exogenous polynucleotide donor sequence. In any of the embodiments, described herein, the host cell can comprise an embryo cell, for example a one or more mouse, rat, rabbit or other mammal cell embryo (e.g., a non-human primate).

In another aspect, described herein is a method for cleaving one or more LRRK2 or SCNA genes in a cell, the method comprising: (a) introducing, into the cell, one or more polynucleotides encoding one or more ZFNs or TALENs that bind to a target site in the one or more genes under conditions such that the ZFN(s) is (are) or TALENs is (are) expressed and the one or more genes are cleaved.

In another embodiment, described herein is a method for modifying one or more LRRK2 or SCNA gene sequence(s) in the genome of cell, the method comprising (a) providing a cell comprising one or more LRRK2 or SCNA sequences; and (b) expressing first and second zinc-finger nucleases (ZFNs) or TALENs in the cell, wherein the first ZFN or TALEN cleaves at a first cleavage site and the second ZFN or TALEN cleaves at a second cleavage site, wherein the gene sequence is located between the first cleavage site and the second cleavage site, wherein cleavage of the first and second cleavage sites results in modification of the gene sequence by non-homologous end joining and/or homology directed repair. Optionally, the cleavage results in insertion of an exogenous sequence (transgene) which also has been introduced into the cell. In certain embodiments, the exogenous sequence comprises a marker, for example a selectable marker (e.g., antibiotic resistance) and/or a recombinase site (e.g., a Cre-recombinase site such as loxP). In other embodiments, the exogenous sequence does not include a reporter (e.g., selection marker). In still other embodiments, non-homologous end joining results in a deletion between the first and second cleavage sites. The size of the deletion in the gene sequence is determined by the distance between the first and second cleavage sites. Accordingly, deletions of any size, in any genomic region of interest, can be obtained. Deletions of 1, 5, 10, 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein. Using these methods and compositions, constructs encoding mutant LRRK2 or SCNA proteins may be developed that lack one or more of the known domains. These constructs can then be used to study the function of the protein within a cell and/or animal.

In another aspect, specific mutations associated with PD can be corrected to understand the function of the gene that harbors the mutation, and/or to discover phenotypes associated with the correction of the mutant gene. Such an understanding then can be used to design cells, cell lines and transgenic animals for use in drug screening and drug discovery.

In another aspect, site specific mutations in a gene associated with PD can be constructed to model known or novel mutations. For example, the A53T, A30P, and E46K mutations in SCNA can be constructed to develop a cell, cell line, primary cell, or transgenic animal bearing these mutations, either as single mutations or in combination. The G2019S mutation in LRRK2 can be similarly constructed in a cell, cell line, primary cell or transgenic animal. In one embodiment, a cell, cell line or transgenic animal carrying a heterozygous genotype for the selected gene is constructed, while in another embodiment, a homozygous cell, cell line or transgenic animal is made carrying two mutant copies in both alleles of a desired locus. The sequences encoding the PD-related mutation(s) may be integrated into any wild-type gene (e.g., the wild-type gene corresponding to the mutant sequence such as a mutant SCNA into a wild-type SCNA gene) or into any mutant gene. In a further embodiment, a cell, cell line or transgenic animal is made comprising two or more mutations in genes associated with PD at separate loci, (e.g. LRRK2 and SCNA) and these cells, cell lines or transgenic animals may be heterozygous for a mutation in each loci, homozygous and all combinations thereof.

In another aspect, described herein are methods of inactivating a LRRK2 or SCNA gene in a cell by introducing one or more proteins, polynucleotides and/or vectors into the cell as described herein. In any of the methods described herein the ZFNs or TALENs may induce targeted mutagenesis, targeted deletions of cellular DNA sequences, and/or facilitate targeted recombination at a predetermined chromosomal locus. Thus, in certain embodiments, the ZFNs or TALENs delete or insert one or more nucleotides of the target gene. In some embodiments the LRRK2 or SCNA gene is inactivated by ZFN or TALEN cleavage followed by non-homologous end joining (NHEJ). In other embodiments, a genomic sequence in the target gene is replaced, for example using a ZFN or TALEN (or vector encoding said ZFN or TALEN) as described herein and a "donor" sequence that is inserted into the gene following targeted cleavage with the ZFN or TALEN. Thus, also provided by the invention is a donor nucleic acid, which can comprise a transgene or sections thereof, or regions of homology with genome flanking the nuclease cleavage site, or nucleic acid sequences relating to gene elements such as promoter sequences and the like. The donor sequence may be present in the ZFN or TALEN vector, present in a separate vector (e.g., Ad or LV vector) or, alternatively, may be introduced into the cell using a different nucleic acid delivery mechanism. In one aspect, the donor sequence causes a known mutation, e.g., A53T, A30P, and E46K alterations in the SCNA protein or the G2019S mutation in the LRRK2 protein. In other aspects, other well known LRRK2 mutation proteins can be constructed through gene modification (e.g. G2385R, R1441C, R1628P and others known in the art).

In another aspect, described herein are methods of correcting a LRRK2 or SCNA gene in a cell by introducing one or more proteins, polynucleotides and/or vectors into the cell as described herein. In any of the methods described herein the ZFNs or TALENs may induce targeted mutagenesis, targeted deletions of cellular DNA sequences, and/or facilitate targeted recombination at a predetermined chromosomal locus. Thus, in certain embodiments, the ZFNs or TALENs delete or insert one or more nucleotides of the target gene. In some embodiments the SCNA gene is corrected by ZFN or TALEN cleavage followed by non-homologous end joining (NHEJ). In other embodiments, a genomic sequence in the target gene is replaced, for example using a ZFN or TALEN (or vector encoding said ZFN or TALEN) as described herein and a "donor" sequence that is integrated into the gene following targeted cleavage with the ZFN or TALEN correcting the sequence of the LRRK2 or SCNA gene. The donor sequence may be present in the ZFN or TALEN vector, present in a separate vector (e.g., Ad or LV vector) or, alternatively, may be introduced into the cell using a different nucleic acid delivery mechanism. In one aspect, the donor sequence corrects a known mutation, e.g., A53T, A30P, and E46K alterations in the SCNA protein or the alteration of an adenine or 'A' guanine to 'G' at position 6055 in a mutant LRRK2 gene to cause the correction of the G2019S mutation. In other aspects, other well known LRRK2 mutation proteins can be corrected through gene modification (e.g. G2385R, R1441C, R1628P and others known in the art).

In some aspects, the cell is a stem cell. Specific stem cell types that may used with the methods and compositions of the invention include embryonic stem cells (ESC), hematopoietic stem cells, nerve stem cells, skin stem cells, muscle stem cells and induced pluripotent stem cells (iPSCs). To investigate the multi-gene aspect of PD, the methods and compositions of the invention can be used in stem cells, e.g. ESC, derived from a variety of differing host cell genetic backgrounds (e.g. differing ethnicities, etc). iPSCs can be derived from patient samples and from normal controls wherein the patient derived iPSCs can be mutated to normal gene sequence at the gene of interest, or normal cells can be altered to the known disease allele at the gene of interest. Panels of these iPSCs can be used to create isogenic cells with both patient and normal cells carrying one or more mutations at their endogenous loci. These cells can be used to create cell lines and/or transgenic animals bearing several mutations of interest to study multi-gene affects of disease severity and possible therapeutic treatments. Other cell types that may be used for these studies are patient derived fibroblasts.

In yet another aspect, described herein is a method for germline disruption of one or more target LRRK2 or SCNA genes, the method comprising modifying one or more LRRK2 or SCNA sequences in the genome of one or more cells of an embryo by any of the methods described herein and allowing the embryo to develop, wherein that the modified gene sequences are present in at least a portion of gametes of the sexually mature animal. In certain embodiments, the animal is a small mammal, such as a rodent or rabbit. In some embodiments, the animal is a non-human primate.

In another aspect, described herein is a method of creating one or more heritable mutant alleles in at least one LRRK2 or SCNA locus of interest, the method comprising modifying one or more LRRK2 or SCNA loci in the genome of one or more cells of an animal embryo by any of the methods described herein; raising the embryo to sexual maturity; and allowing the sexually mature animal to produce offspring; wherein at least some of the offspring comprise the mutant alleles. In certain embodiments, the animal is a small mammal, for example a rabbit or a rodent such as rat, a mouse or a guinea pig. In other embodiments, the animal is a non-human primate.

In any of the methods described herein, the polynucleotide encoding the zinc finger nuclease(s) or TALEN(s) can comprise DNA, RNA or combinations thereof. In certain embodiments, the polynucleotide comprises a plasmid. In other embodiments, the polynucleotide encoding the nuclease comprises mRNA.

In a still further aspect, provided herein is a method for site specific integration of a nucleic acid sequence into a LRRK2 or SCNA locus of a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger or TALE nuclease that recognizes the site of integration in the LRRK2 or SCNA locus, and (b) culturing the embryo to allow expression of the zinc finger or TALE nuclease, wherein a double stranded break introduced into the site of integration by the zinc finger nuclease or TALEN is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a zinc finger or TALE nuclease. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided.

In another aspect provided by the methods and compositions of the invention is the use of cells, cell lines and transgenic animals in the screening of drug libraries and/or other therapeutic compositions (i.e., antibodies, structural RNAs, etc.) for use in treatment of an animal afflicted with PD. Such screens can begin at the cellular level with manipulated cell lines or primary cells, and can progress up to the level of treatment of a whole animal.

A kit, comprising the ZFPs or TALENs of the invention, is also provided. The kit may comprise nucleic acids encoding the ZFPs or TALENs, (e.g. RNA molecules or ZFP or TALEN encoding genes contained in a suitable expression vector), donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 4A shows a gel containing the results of a Tsp45I digest. The introduction of the G209G mutation in the DNA creates a Tsp45I restriction site. In the gel, in the presence of both donor and ZFNs, incorporation of the mutation sequence does occur as demonstrated by the percent of alleles that are now sensitive to the Tsp45I enzyme. FIG. 4B depicts the results of a Cel-I assay (described above) performed on these same samples and demonstrates that the ZFN pair was active because indels are observed in all samples tested that were treated with ZFNs.

FIG. 7A depicts the results using the 27870 ZFN and FIG. 7B depicts the results using the 30888 ZFN. The nucleotide base in both panels indicated by the arrows is position 6055, and the data demonstrates that the 27870 ZFN prefers binding to G at this position while 30888 prefers to bind to A.

DETAILED DESCRIPTION

Figure 1:
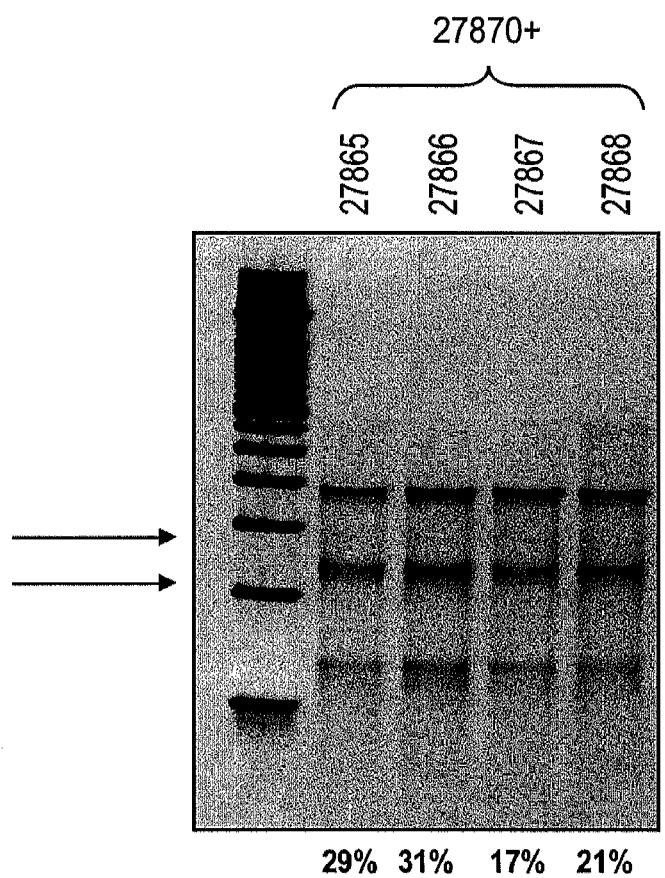
FIG. 1 depicts a gel showing the results of a Cel-I mismatch assay on K562 cells treated with ZFNs targeting the LRRK2 gene. All samples were ZFN pairs where one member of the pair is always the ZFN SBS 27870. The lanes show the results where the other member of the ZFN pair was varied. The Cel-I assay (Surveyor™, Transgenomic) identifies mismatches in a DNA sequence that occur as a result of cleavage followed by repair of the DSB by the NHEJ cellular machinery. In the NHEJ process, small insertions and deletions are often observed (indels), and these create the mismatches identified in the Cel-I assay. At the bottom of each lane is shown the percent of the sequences that display some amount of NHEJ-caused indels at the targeted location. The arrow indicates the band observed from the cleavage by the Surveyor™ enzyme of the mismatch bubble.

Disclosed herein are compositions and methods for treating and/or developing models useful in the treatment of PD. In particular, nuclease-mediated cleavage and integration is used to create or repair known mutations in the LRRK2 or SCNA gene. These compositions and methods can be used to correct or create specific LRRK2 or SCNA mutations in any selected genetic background to allow for study of multifactorial interaction in PD. The invention can be used to create isogenic panels of a set of mutations in LRRK2 or SCNA to allow for controlled study of these mutations, to investigate the link between a certain mutation and cellular dysfunction and to identify phenotypes associated with the mutation or with the correction of the mutation. In addition, any LRRK2 or SCNA mutation can be introduced into patient derived cells, e.g. patient derived induced pluripotent stem cells, to investigate the affects of a certain mutation in a patient cell background. In addition, creation of LRRK2 or SCNA mutants with in-frame alterations is also part of the invention described herein, to allow for fine tuned analysis of the functional domains of this protein. In addition, LRRK2 or SCNA mutations associated with PD can be created within the native gene in model animals (rat, non-human primate, etc.) to generate PD models. These animals may contain one or more inserted LRRK2 or SCNA mutations.

Also described herein are methods and compositions for altering specific LRRK2 or SCNA defects in patient cells. For example, mutated LRRK2 or SCNA genes may be knocked out by use of specific nucleases that will only act on mutant alleles and not act on a wild type gene sequence. Knock out of a specific gene may be a result of cleavage followed by NHEJ, or by cleavage at two loci within the gene to delete a large portion of the gene, or by cleavage followed by targeted integration of an oligonucleotide or larger donor DNA. Alternatively, specific LRRK2 or SCNA mutations in patient cells may be corrected using the methods and compositions of the invention. These corrected cells may then be re-introduced into the patient for treatment of the disease.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant $K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains or TALEN can be "engineered" to bind to a predetermined nucleotide sequence, for example via engineering (altering one or more amino acids) of the recognition helix region of a naturally occurring zinc finger or by engineering the RVDs of a TALEN protein. Therefore, engineered zinc finger proteins or TALENs are proteins that are non-naturally occurring. Non-limiting examples of methods for engineering zinc finger or TALEN proteins are design and selection. A designed zinc finger or TALEN protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger or TALEN protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013, 453; U.S. Pat. No. 6,200,759; WO 95/19431; WO 96/06166;

WO 98/53057; WO 98/54311; WO 00/27878; WO 01/60970 WO 01/88197 and WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene," "reporter sequence," "marker gene" or "marker sequence" refers to any sequence that produces a protein product that is easily measured, preferably although not necessarily in a routine assay. Suitable reporter/marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Nucleases

Described herein are compositions, particularly nucleases, which are useful in integration of a peptide fusion inhibitor into a cell surface receptor (e.g., viral receptor) or disruption of the cell surface receptor to inhibit entry of macromolecules that bind to the cell surface receptor. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-SceI, I-SceIV, I-CsmI, IPanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441: 656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove, (2009) *Science* 326:1501 and Boch et al (2009) *Science* 326: 1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). Christian et al ((2010)<Genetics epub 10.1534/genetics.110.120717). See, also, U.S. Patent Publication No. 20110301073, incorporated by reference in its entirety herein.

In certain embodiments, the DNA binding domain comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534, 261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The zinc finger proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases, Cold Spring Harbor Laboratory Press,* 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/

0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FoId), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US U.S. Patent Publication No. 2011/0201055).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and U.S. Publication No. 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073, incorporated by reference in its entirety herein.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Application No. 20110287512.

Donors

It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the cell surface receptor with which the peptide fusion inhibitor is expressed. However, it will be apparent that the donor may comprise a promoter and/or enhancer, for example a constitutive promoter or an inducible or tissue specific promoter that drives expression of the function peptide fusion inhibitor upon integration.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (nuclease-encoding and/or peptide fusion inhibitor-encoding) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Parkinson's Disease and Genetic Mutations

As described above, mutations in several genes are found in both familial and sporadic cases of PD. The instant invention describes methods and compositions that can be used to introduce or repair such mutations. Shown below is a table of exemplary genes and loci that have been associated with PD in some manner.

TABLE 1

Exemplary genes and loci linked with PD

| Locus | Gene | Chromosome | Inheritance/clinical phenotype |
|---|---|---|---|
| PARK1/ PARK4/ SCNA | α-synuclein | 4q21 | AD and sporadic/early onset PD |
| PARK2 | Parkin | 6q25.2-q27 | AR and sporadic/early onset PD |
| PARK3 | unknown | 2p13 | AD/late onset PD, no caustative gene identified |
| PARK5 | UCH-L1 | 4p14 | AD/late onset PD, reported in a PD sibling pair |
| PARK7 | DJ-1 | 1p36 | AR/early onset PD |
| PARK8 | LRRK2 | 12p11.2-q13.1 | AD and sporadic/late onset PD |
| PARK9 | ATP13A2 | 1P36 | AR/early onset PD |
| PARK10 | unknown | Xq21-q25 | Unknown, no causative gene identified |
| PARK11 | GIGYF2 | 2q36-q37 | AD/late onset PD, pathogenicity unknown |
| PARK12 | unknown | Xq21-q25 | Unknown, no causitive gene identified |
| PARK13 | HTRA2 | 2p13 | Unknown, no causitive gene identified |
| PARK14 | PLA2G6 | 22q12-q13 | AR/L-dopa responsive dystonia-parkinsonism |
| PARK15 | FBX07 | 22q12-q13 | AR/parkinsonism-pyramidal syndrome |

Notes:
AD, autosomal dominant; AR, autosomal recessive, UCHL1, ubiquitin carboxy-terminal hydroplast L1; PINK1, PTEN-induced kinase 1; ATP13A2, ATPase type 13A2; GIGYF2, GRB10-interacting GYF protein 2; HTRA2, HtrA serine peptidase 2; PLA2G6, group VI phospolipase A2; FBX07, F-box protein 7

In particular, specific mutations at the LRRK2 gene that have been proven shown to be pathogenic in the development of PD include Y1699C, R1441C, R1441H, R1441H, 11371V, Y1699G, G2019S, 12020T, and G2385R. Mutations within LRRK2 that are potentially pathogenic include E334K, Q1111H, I1192V, I1122V, S1228T, A1442P, L1719F, and T2356I. Those mutations that are associated with an increased risk of developing PR are R1628P and G2385R (see Kumari, ibid). Specific mutations at the SCNA gene that have been shown to be pathogenic in the development of PD include A53T, A30P, and E46K. Thus, the methods and compositions of the instant invention are useful for repairing such mutations in LRRK2 or SCNA or other genes associated with PD, and are useful for developing cell and transgenic animal models to study the intracellular pathology associated with the various mutations and for studying the whole organism consequences of these mutations.

Additionally, cells, cell lines and transgenic animals are useful for drug development. Such cells and animals may reveal phenotypes associated with a particular mutation (e.g. LRRKs G2019S or SCNA A53T, A30P, and E46K alterations) or with its correction, and may be used to screen drugs that will interact either specifically with the mutation(s) in question, or that are useful for treatment of the disease in an afflicted animal. Therapeutically, iPSCs can be derived ex vivo from a patient afflicted with a known genetic mutation associated with PD, and this mutation can be corrected using ZFN- or TALEN-mediated gene correction. The corrected iPSCs can then be differentiated into dopaminergic neurons and reimplanted into the patient.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains or TALENs.

EXAMPLES

Example 1

Nucleases Specific for LRRK2 and SCNA

ZFN pairs targeting the human LRRK2 gene in proximity of the rs34637584 SNP were used to test the ability of these ZFNs to induce DSBs at a specific target site. The amino acid sequence of the recognition helix region of the indicated ZFNs are shown below in Tables 2 and 4 and their target sites shown in Tables 3 and 5 ((DNA target sites indicated in uppercase letters; non-contacted nucleotides indicated in lowercase). The Cel-I assay (Surveyor™, Transgenomics. Perez et al. (2008) Nat. Biotechnol. 26: 808-816 and Guschin et al. (2010) Methods Mol Biol. 649:247-56), was used where PCR-amplification of the target site was followed by quantification of insertions and deletions (indels) using the mismatch detecting enzyme Cel-I (Yang et al. (2000) Biochemistry 39, 3533-3541) which provides a lower-limit estimate of DSB frequency. Two days following transfection of the ZFN expression vector, genomic DNA was isolated from K562 cells using the DNeasy kit (Qiagen). In these experiments, all ZFN pairs were ELD/KKR FokI mutation pairs (described above).

Results from the Cel-I assay are shown in FIG. 1, and demonstrate that the ZFNs shown below are capable of inducing cleavage at their respective target sites.

TABLE 3

Target sites for LRRK2-specific ZFNs

| ZFN Name | Target Site |
|---|---|
| SBS 27870 | gcAAAGATtGCTGACtACGGCAttgctc (SEQ ID NO: 17) |
| SBS 27865 | tgATGGCAGCATTGGGAtacagtgtgaa (SEQ ID NO: 18) |
| SBS 27866 | tgATGGCAGCATTGGGAtacagtgtgaa (SEQ ID NO: 18) |
| SBS 27867 | tgATGGCAGCATTGGGAtacagtgtgaa (SEQ ID NO: 18) |
| SBS 27868 | tgATGGCAGCATTGGGAtacagtgtgaa (SEQ ID NO: 18) |
| SBS 30886 | tgATGGCAGCATTGGGAtacagtgtgaa (SEQ ID NO: 18) |
| SBS 30888 | gcAAAGATtGCTGACtACAGCAttgctc (SEQ ID NO: 46) |

ZFN pairs targeting the position nucleotide position 209 of exon 3 in the human SCNA gene were used to test the ability of these ZFNs to induce DSBs at the specific target site in K562 cells as described above. The ZFNS and their target sites are shown below in Tables 4 and 5.

Figure 2:
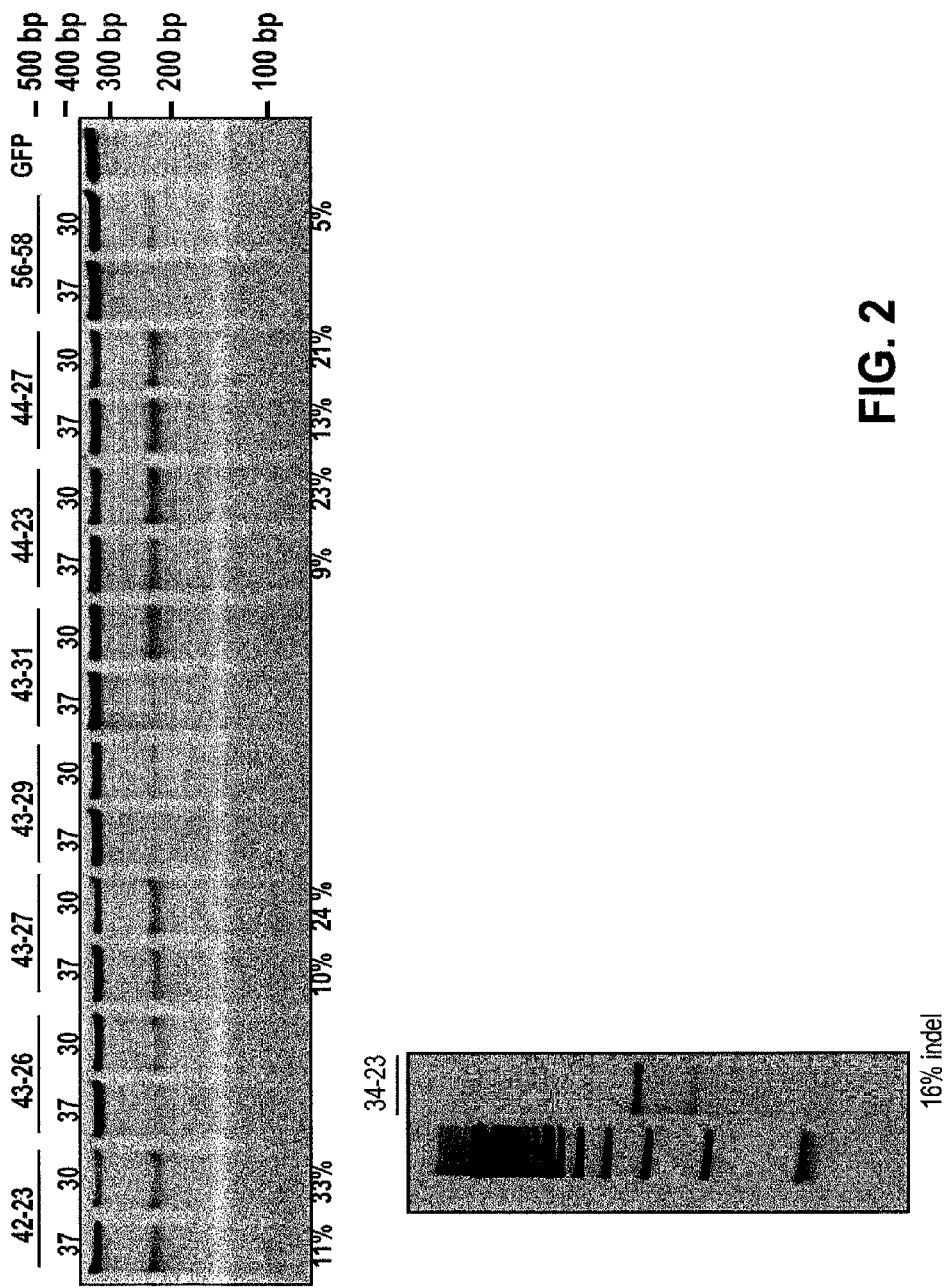
FIG. 2 shows a gel wherein screening of ZFNs directed against nucleotide base 209 in exon 3 of human alpha-synuclein (SNCA) was performed. The indicated ZFN pairs were transiently transfected into K562 cells, genomic DNA was isolated 48 hrs later, and the frequency of target locus disruption was measured by the Surveyor/Cel-1 assay. The frequency of gene disruption of the most efficient ZFN pairs is indicated below each lane.

Samples of the nucleofected cell pools were used to PCR amplify the region around the DSB, and then subjected to the Cel-I assay. The data are presented in FIG. 2 and demonstrate that these ZFNs pairs were capable of inducing DSBs at the target sequence. All ZFN pairs contained ELD/KKR FokI pairs (see above).

TABLE 2

LRRK2-specific ZFNs

| ZFN name | F1 | F2 | F3 | F4 | F5 | F6 |
|---|---|---|---|---|---|---|
| SBS 27870 | QSGDLTR (SEQ ID NO: 1) | RNDILAS (SEQ ID NO: 2) | DRSNLSR (SEQ ID NO: 3) | LRQDLKR (SEQ ID NO: 4) | TSGNLTR (SEQ ID NO: 5) | QSNQLRQ (SEQ ID NO: 6) |
| SBS 27865 | QSGHLSR (SEQ ID NO: 7) | RSDSLSV (SEQ ID NO: 8) | QSSDLRR (SEQ ID NO: 9) | QSGDLTR (SEQ ID NO: 1) | RKDPLKE (SEQ ID NO: 10) | N/A |
| SBS 27866 | QSGHLSR (SEQ ID NO: 7) | RSDSLSV (SEQ ID NO: 8) | QSSDLRR (SEQ ID NO: 9) | QSGDLTR (SEQ ID NO: 1) | RRDPLIN (SEQ ID NO: 11) | N/A |
| SBS 27867 | QSGHLAR (SEQ ID NO: 12) | RKWTLQG (SEQ ID NO: 13) | QSSDLSR (SEQ ID NO: 14) | QWSTRKR (SEQ ID NO: 15) | RSDALTQ (SEQ ID NO: 16) | N/A |
| SBS 27868 | QSGHLAR (SEQ ID NO: 12) | RKWTLQG (SEQ ID NO: 13) | QSGDLTR (SEQ ID NO: 1) | QSGDLTR (SEQ ID NO: 1) | RKDPLKE (SEQ ID NO: 10) | N/A |
| SBS 30886 | QSGHLSR (SEQ ID NO: 7) | RSDSLSA (SEQ ID NO: 44) | QSGDLTR (SEQ ID NO: 1) | QSGDLTR (SEQ ID NO: 1) | RKDPLKE (SEQ ID NO: 10) | N/A |
| SBS 30888 | QSGDLTR (SEQ ID NO: 1) | QWGTRYR (SEQ ID NO: 45) | DRSNLSR (SEQ ID NO: 3) | LRQDLKR (SEQ ID NO: 4) | TSGNLTR (SEQ ID NO: 5) | QSNQLRQ (SEQ ID NO: 6) |

TABLE 4

SCNA-specific ZFNs

| ZFN Name | F1 | F2 | F3 | F4 | F5 | F6 |
|---|---|---|---|---|---|---|
| SBS 26343 ("43") | IRDYLIK (SEQ ID NO: 19) | RPYTLRL (SEQ ID NO: 20) | QSGDLTR (SEQ ID NO: 1) | HRSDRTR (SEQ ID NO: 21) | QSGALAR (SEQ ID NO: 22) | RSDNLRE (SEQ ID NO: 23) |
| SBS 26344 ("44") | QKRNRTK (SEQ ID NO: 24) | RPYTLRL (SEQ ID NO: 20) | QSGDLTR (SEQ ID NO: 1) | HRSDRTR (SEQ ID NO: 21) | QSGALAR (SEQ ID NO: 22) | RSDNLRE (SEQ ID NO: 23) |
| SBS 26323 ("23") | DSSDRKK (SEQ ID NO: 25) | DQSNLRA (SEQ ID NO: 26) | QSGDLTR (SEQ ID NO: 1) | ASHNLRT (SEQ ID NO: 27) | DQSNLRA (SEQ ID NO: 26) | N/A |
| SBS 26327 ("27") | DSSDRKK (SEQ ID NO: 25) | DQSNLRA (SEQ ID NO: 26) | QSGDLTR (SEQ ID NO: 1) | TSHNRNA (SEQ ID NO: 28) | DQSNLRA (SEQ ID NO: 26) | N/A |
| SBS 26326 ("26") | DRSYRNT (SEQ ID NO: 29) | QSNDLNS (SEQ ID NO: 30) | QSGDLTR (SEQ ID NO: 1) | TSHNRNA (SEQ ID NO: 28) | DQSNLRA (SEQ ID NO: 26) | N/A |
| SBS 25356 ("56") | DQSNLRA (SEQ ID NO: 26) | QSGDLTR (SEQ ID NO: 1) | ASHNLRT (SEQ ID NO: 27) | DQSNLRA (SEQ ID NO: 26) | N/A | N/A |
| SBS 25358 ("58") | TSGSLSR (SEQ ID NO: 31) | WRSSLTA (SEQ ID NO: 32) | GRDSLIE (SEQ ID NO: 33) | RSSDLSR (SEQ ID NO: 34) | QSGALAR (SEQ ID NO: 22) | RSDNLRE (SEQ ID NO: 23) |
| SBS 26329 ("29") | DQSNLRA (SEQ ID NO: 26) | QSGDLTR (SEQ ID NO: 1) | TSHNRNA (SEQ ID NO: 28) | DRSNRKT (SEQ ID NO: 35) | N/A | N/A |
| SBS 26334 ("34") | TSGSLSR (SEQ ID NO: 31) | WRSSLTA (SEQ ID NO: 32) | QSGDLTR (SEQ ID NO: 1) | HRSDRTR (SEQ ID NO: 21) | QSGALAR (SEQ ID NO: 22) | RSDNLRE (SEQ ID NO: 23) |
| SBS 26331 ("31") | DSSDRKK (SEQ ID NO: 25) | DQSNLRA (SEQ ID NO: 26) | QSGDLTR (SEQ ID NO: 1) | TSHNRNA (SEQ ID NO: 28) | DRSNRKT (SEQ ID NO: 35) | N/A |

TABLE 5

Target sites of SCNA-specific ZFNs

| ZFN Name | Target Site |
|---|---|
| SBS 26343 ("43") | aaCAGGTAaGCTCCATTGTGCttatatc (SEQ ID NO: 36) |
| SBS 26344 ("44") | aaCAGGTAaGCTCCATTGTGCttatatc (SEQ ID NO: 36) |
| SBS 26323 ("23") | caCACCATGCAcCACTCCctccttggtt (SEQ ID NO: 37) |
| SBS 26327 ("27") | caCACCATGCAcCACTCCctccttggtt (SEQ ID NO: 37) |
| SBS 26326 ("26") | caCACCATGCAcCACTCCctccttggtt (SEQ ID NO: 37) |
| SBS 25356 ("56") | caCACCATGCAcCACTccctccttggtt (SEQ ID NO: 37) |
| SBS 25358 ("58") | aaCAGGTAaGCTCCAtTGTGCTtatatc (SEQ ID NO: 36) |
| SBS 26329 ("29") | caCACCATGCAcCACTccctccttggtt (SEQ ID NO: 37) |
| SBS 26334 ("34") | aaCAGGTAaGCTCCAtTGTGCTtatatc_ (SEQ ID NO: 36) |
| SBS 26331 ("31") | caCACCATGCAcCACTCCctccttggtt (SEQ ID NO: 37) |

Example 3

Insertion of a 6055G>A Mutation into a Wild Type LRRK2 Allele

It would be advantageous to be able to create a mutant allele in the LRRK2 in any desired cell type to allow for study of the mutation in a variety of genotypic backgrounds.

Accordingly, the LRRK2-specific ZFNs were used to induce targeted integration of the sequences encoding this mutation within wild type cells using a donor DNA including the mutation. For donor, 1000 bp of a PCR product generated by performing a PCR reaction on patient DNA carrying the mutation was used, and is shown below, where the mutation is indicated in bold and underlined font:

```
                                           (SEQ ID NO: 38)
5' AGCTGAGCTAAACCTCTATGTGGTTTTAGGAAAATCAAAACTATTA

AATAAATGGCAAGTACAACAAAATCCCATCAATTCTTATTTAACATACT

TACATTTTGAAATAGTTAAAATATTCATATGATCATTGAGAGAATTCAG

AATTGCCTTTAAGTAATTGTTCACATATACAAAAGAAAAGTCTCCAAAA

ATTGGGTCTTTGCCTGAGATAGATTTGTCTTAAAATTGAAATCATTCAC

TTATCAGATTTGACCCTTTTTTAAAGCATAACTTTGCTGTGTAATATTA

GACTTATATGTTTTGATTTCCTTCTACAATATCTCTTAACTTTAAGGGA

CAAAGTGAGCACAGAATTTTTGATGCTTGACATAGTGGACATTTATATT

TAAGGAAATTAGGACAAAAATTATTATAATGTAATCACATTTGAATAAG

ATTTCCTGTGCATTTTCTGGCAGATACCTCCACTCAGCCATGATTATAT

ACCGAGACCTGAAACCCCACAATGTGCTGCTTTTCACACTGTATCCCAA
```

-continued
```
TGCTGCCATCATTGCAAAGATTGCTGACTACAGCATTGCTCAGTACTGC

TGTAGAATGGGGATAAAAACATCAGAGGGCACACCAGGTAGGTGATCAG

GTCTGTCTCATAATTCTATCTTCAGGATGGATAACCACTGACCTCAGAT

GTGAGTTCAGAAGAGTCAAAAGGAAAACAGAGTCTATCACATTGTGAAC

AGAGGTTTATTTTGTGAAAAAATGCAAGCATCACATTGTGATTTTTATC

TTGTATTTTGTAGGAAAAAAACAATTGATGTAATTTTTCAGGGCAAAAA

ACTGAATAAAAGAAGAGAATGTTTGATATCAAGTTATATGTTTTAAAG

TTAGATTTGTAGATTCTTTAGATACTCTAGAGGTCATAAAAAGTAACAG

ACAAAACTTTAGTCTAGGTATTGTTGGCACTTGTGAGGCAAATCAAATT

CAGGTCCACAAATTCTTTTTC 3'
```

The LRRK2-specific ZFNs were nucleofected into K562 cells along with varying amounts of donor (from 0.5 μg-2.0 μg) according to standard protocol as described above. DNA was then isolated from the transfectants and used for a PCR reaction where a first PCR reaction was done to isolate the genomic DNA. This reaction was then diluted and subjected to another PCR yielding an approximately 320 bp product that was then subjected to SfcI digestion which exclusively recognizes the mutant sequence and creates a faster moving product on a gel.

Figure 3:
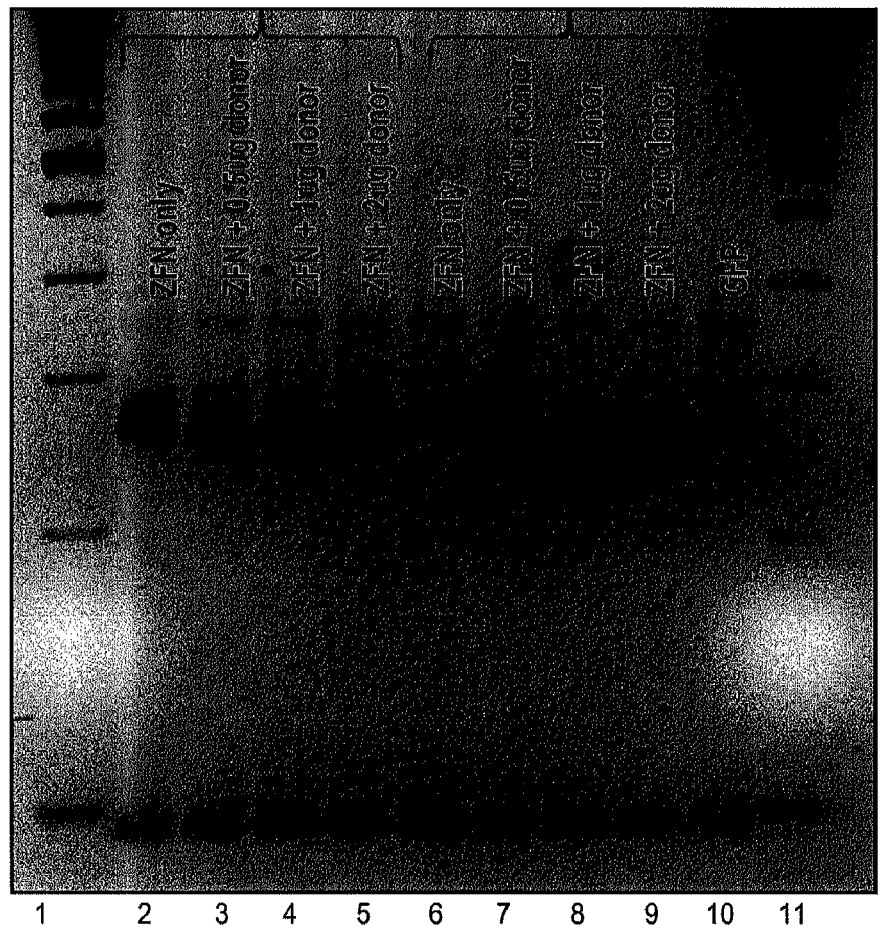
FIG. 3 shows a gel depicting results of an experiment designed to knock in the 6055G>A mutation to create the G2019S allele in the LRRK2 gene. In this experiment, ZFNs and donor plasmid containing the sequence for the mutated allele were nucleofected into K562 cells. The DNA was isolated, and a PCR reaction was performed to amplify the region around the mutant locus. The product was then digested with SfcI, and run on a gel. The presence of the mutation results in a faster migrating band as described above. The faster migrating band is indicated with an arrow while the wild type band is indicated with an open triangle.

The results are depicted in FIG. 3. Controls included nucleofection with the ZFNs only (lanes 2 and 6) and nucleofection with a plasmid encoding GFP (lane 10). The mutant digestion bands are evident in lanes 3, 4 and 7, (indicated with an arrow) demonstrating that these clones now carry the 6055 G>A mutation associated with the G2019S LRRK2 mutant allele. The band from the wild type gene is indicated with an open triangle.

Figure 7:
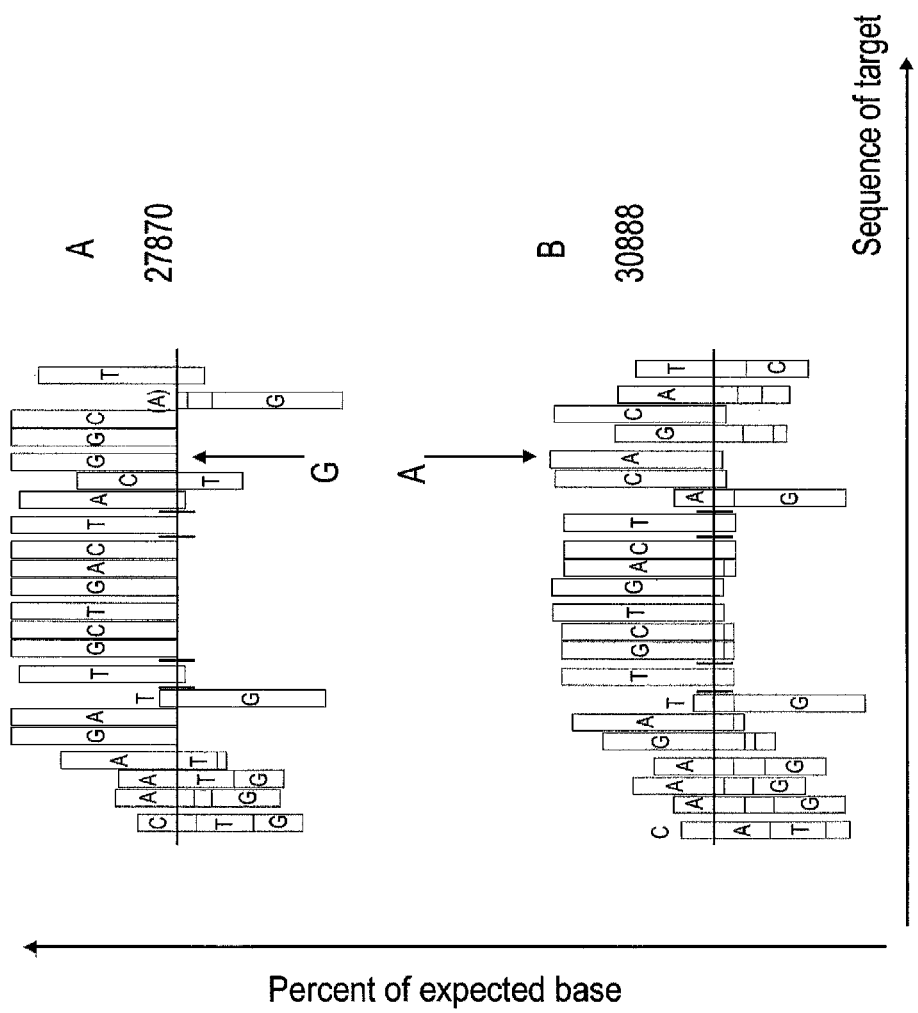
FIG. 7, panels A and B, depict the results of a SELEX assay designed to demonstrate the target sequence binding preference for a given zinc finger protein. In these diagrams, the binding results for each base of the expected target sequence is shown above the horizontal line, while the binding results for each position to other bases is shown below the line. The larger the block of each base type (A, C, G or T), the greater the preference for that base.
Figure 8:
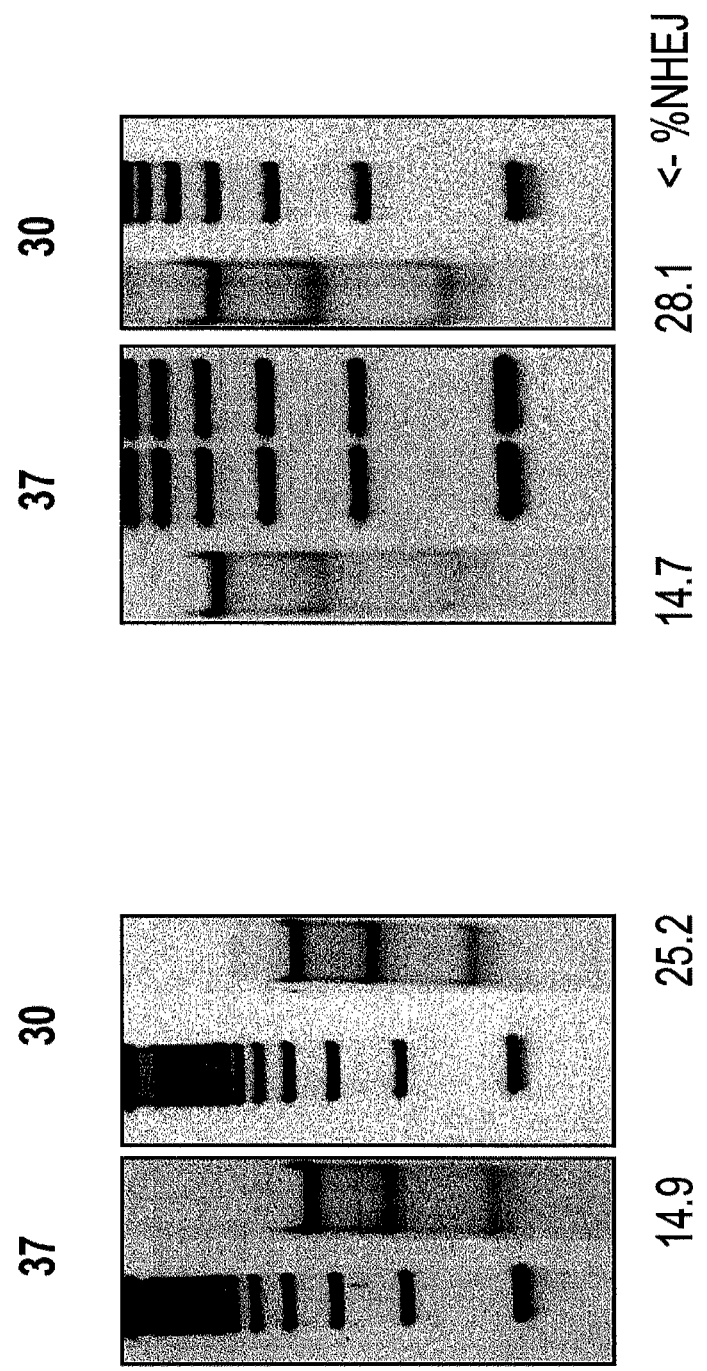
FIG. 8 depicts gels demonstrating the percent of gene modification in K562 cells by the Cel I assay described above using the 30885/88 or the 27866/70 ZFN pairs. Both pairs are able to elicit gene modification at the target in the range of 14-28 percent ("% NHEJ). This assay was carried out in both the standard (37°) and transient hypothermic (30°) conditions.

ZFNs specific for either the wild type LRRK2 target sequence or the mutant target sequence were developed. As shown below, the 6055 G>A mutation in LRRK2 results in the expression of the mutant G2019S protein. Thus, it is of interest to develop ZFNs which are capable of enhanced cleavage on the mutant 6055 locus in comparison with the wild type 6055 locus. The two sequences are shown below, where the "Wildtype" sequence additionally has a silent mutation resulting in the creation of an AciI restriction site inserted:

ZFNs were developed with an increased affinity for the mutant sequence that ZFN 27870 binds to in the wild type LRRK2 gene. The new ZFP demonstrated specificity in a SELEX assay (as described in Perez et al (2008) supra) for A in the 6055 location rather than the wild type G (see, FIG. 7). These ZFNs were then used to test DNA cutting in vitro in K562 cells and were found to cut the LRRK2 locus using the Cel I assay as described above, where the assay was also conducted using a transient hypothermic shock (see co-owned US Patent publication 20110129898). The 30886/30888 pair has an enhanced affinity for the mutant 6055 locus but is still able to cleave the wild type gene in these conditions (see, FIG. 8).

Example 4

Insertion of a Mutation into a Wild Type SNCA Allele

For the development of model systems, it would be advantageous to insert a mutation into a PD-associated gene in any cell of interest. Accordingly, K562 cells were nucleofected as described above with 0.4 ug of each plasmid encoding ZFNs 26323/26334 (ELD/KKR) targeting the SNCA locus, along with increasing amounts of donor DNA. The donor used comprised approximately 1000 bp homology with the SNCA locus and contained the G209A mutation encoding the A53T SNCA mutation. The donor sequence is shown below where the G2019A mutation is indicated in bold/underline.

```
                                      (SEQ ID NO: 39)
CTCGTGATCTGCCCACCTCGGCCTCCCAAATTGCTGGGATTACAGGCAT

GAGCCACTGCGCCCAGCCTAAAATGTTTTTTTTACATAATGGGTGTTCA

GCACATGTTAAAGCCTTCTCTCCATCCTTCTTCCCTTTTGTTTCATGGG

TTGACTGATCTGTCTCTAGTGCTGTACTTTTAAAGCTTCTACAGTTCTG

AATTCAAAATTATCTTCTCACTGGGCCCCGGTGTTATCTCATTCTTTTT

TCTCCTCTGTAAGTTGACATGTGATGTGGGAACAAAGGGGATAAAGTCA

TTATTTTGTGCTAAAATCGTAATTGGAGAGGACCTCCTGTTAGCTGGGC

TTTCTTCTATTTATTGTGGTGGTTACTGGAGTTCCTTCTTCTAGTTTTA
```

```
                                              (SEQ ID NO: 47)
                                  Sfc I
G2019S                         27870
CTTTTCACACTGTATCCCAATGCTGCCATCATTGCAAAGATTGCTGACTACAGCATTGCTCAGTACT (SEQ ID NO: 48)
GAAAAGTGTGACATAGGGTTACGACGGTAGTAACGTTTCTAACGACTGATGTCGTAACGAGTCATGA
                27866

(SEQ ID NO: 49)
"Wildtype"                     27870
CTTTTCACACTGTATCCCAATGCTGCCATCATTGCAAAGATTGCTGACTACGGCATTGCTCAGTACT (SEQ ID NO: 50)
GAAAAGTGTGACATAGGGTTACGACGGTAGTAACGTTTCTAACGACTGATGCCGTAACGAGTCATGA
               27866                        Aci I
                      BsrDI
```

-continued

```
GGATATATATATATATATTTTTTTCTTTCCCTGAAGATATAATAATATATA

TACTTCTGAAGATTGAGATTTTTAAATTAGTTGTATTGAAAACTAGCTA

ATCAGCAATTTAAGGCTAGCTTGAGACTTATGTCTTGAATTTGTTTTTG

TAGGCTCCAAAACCAAGGAGGGAGTGGTGCATGGTGTGACAACAGGTAA

GCTCCATTGTGCTTATATCCAAAGATGATATTTAAAGTATCTAGTGATT

GTGTGGCCCAGTATTCAAGATTCCTATGAAATTGTAAAACAATCACTGA

GCATTCTAAGAACATATCAGTCTTATTGAAACTGAATTCTTTATAAAGT

ATTTTTAAATAGGTAAATATTGATTATAAATAAAAAATATACTTGCCAA

GAATAATGAGGGCTTTGAATTGATAAGCTATGTTTAATTTATAGTAAGT

GGGCATTTAAATATTCTGACCAAAAATGTATTGACAAACTGCTGACAAA

AATAAAATGTGAATATTGCCATAATTTTAAAAAAAGTAAAATTTCTGTT

GATTACAGTAAAATATTTTGACCTTAAATTATGTTGATTACAATATTCC

TTTGATAATTCAGAGTGCATTTCAGGAAACACCCTTGGACAG
```

PCR was performed on the genomic DNA following nucleofection using the primer pairs described below that have homology to regions outside the target domain (making sure not to amplify the donor DNA that may be unintegrated). The primers were as shown below and amplified a 1929 bp sequence:

```
                                     (SEQ ID NO: 40)
   F: AAG ATT CCC ATA TCA TTG TCC TC (SEQ ID NO: 41)
   R: GGT TTG GAA GAA ATT CTG ATC CTG
```

The introduction of the G209A mutation results in generation of a Tsp45I restriction site, thus successful incorporation of the donor will result in a Tsp45I sensitive PCR product. Thus, the PCR product was digested with the Tsp45I restriction enzyme, and the product ran on a 1% agarose gel. The expected band sizes of the digestion products are 1018 and 912 bp. In a parallel experiment, the PCR product was diluted, and used as a template for the Cel-1 assay as described previously, using the Cel-I primers shown below.

```
                                     (SEQ ID NO: 42)
   F: AAA CTA GCT AAT CAG CAA TTT AAG GC (SEQ ID NO: 43)
   R: AGC CCT CAT TAT TCT TGG CA
```

Figure 4:
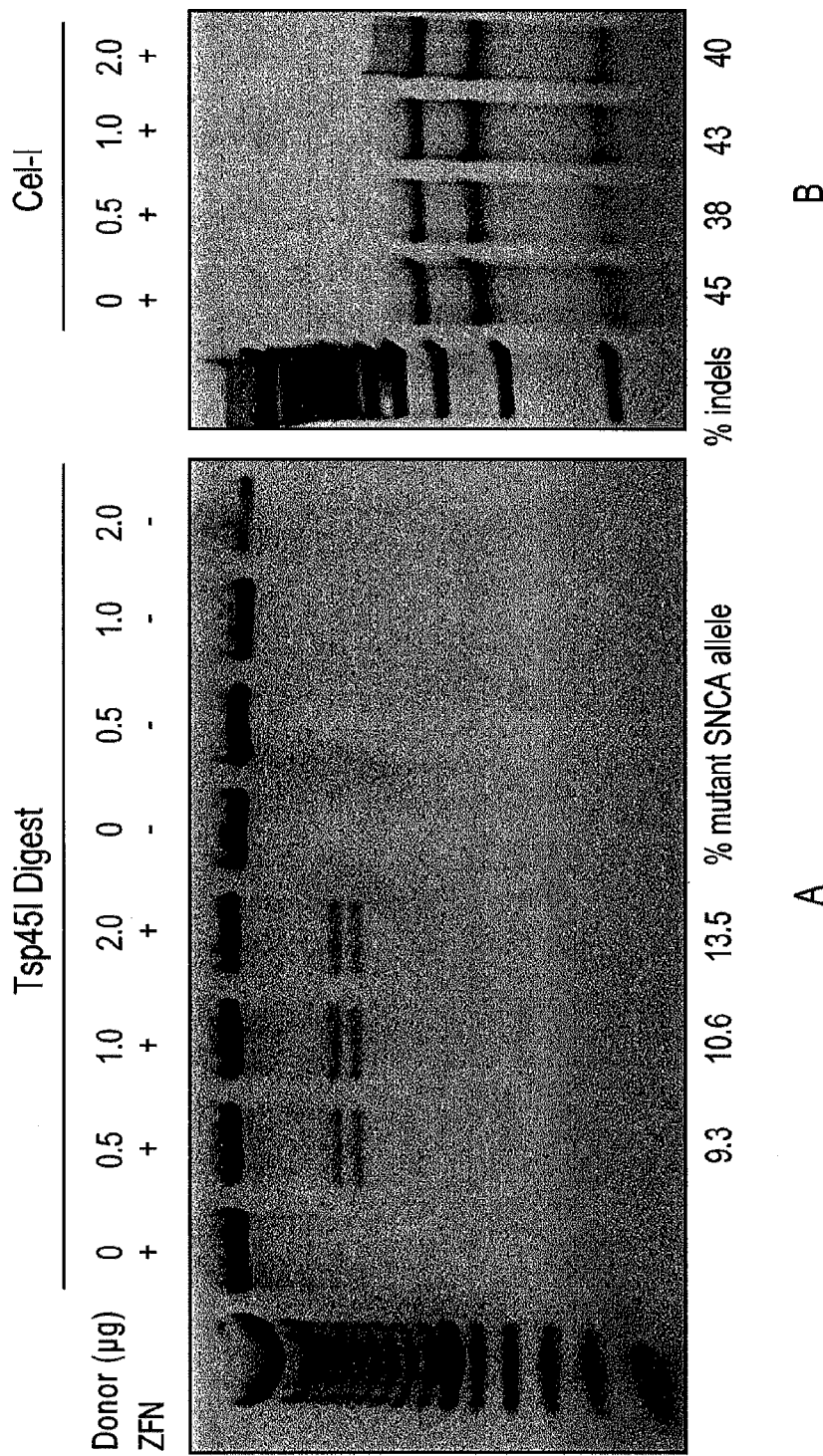
FIG. 4, panels A and B, are gels depicting the results of an experiment designed to knock in the synuclein G209A mutation (encoding the PD-associated A53T mutation in the SCNA protein) in K562 cells.

The results of these experiments are shown in FIG. 4. FIG. 4A shows the results of the Tsp45I digest on samples that were nucleofected with either donor+ZFN, or donor alone. The results demonstrated that up to 13.5% of the SCNA alleles were mutated in the presence of the donor DNA. FIG. 4B shows the results of the Cel-I assay performed on these same samples. These data demonstrate that the ZFNs were active in these samples (e.g., up to 45% indels present in the absence of donor). Thus, the PD associated A53T mutation in SCNA was successfully introduced into these cells.

Example 5

Insertion of Disease-Causing A53T (G209) α-Synuclein Mutation into hESCs

Figure 5:
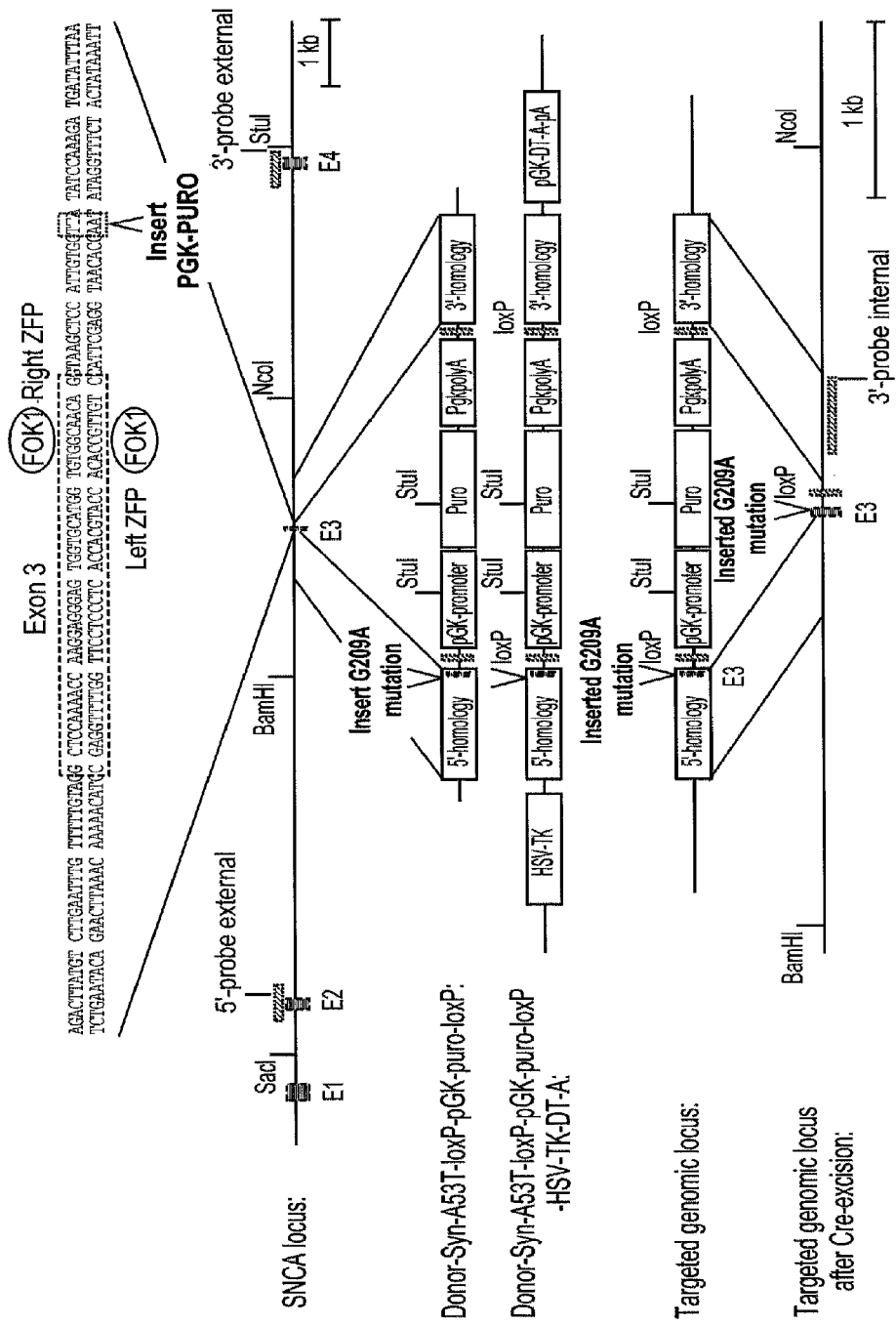
FIG. 5 is a schematic depicting the genomic α-synuclein locus (SNCA) and the targeting strategy showing exons (blue boxes), restriction sites and location of external and internal southern blot probes (red bars). Enlarged sequence (SEQ ID NO: 52) indicates ZFNs induced cut site at base 209 in exon 3 of α-synuclein (red base pair) and insertion site of loxP-site-flanked pGK-puro selection cassette (red box). Shown below is a schematic of the donor plasmid design for either normal selection (Syn-A53T-loxP-pGK-puro-loxP) or positive-negative selection (Syn-A53T-loxP-pGK-puro-loxP-HSV-TK-DT-A) and targeted genomic locus before and after Cre-excision of the selection cassette. The donor plasmids comprise ~600 bp homology on each side of the ZFN cut. pGK-promoter, phosphoglycerol kinase promoter; puro, puromycin resistance gene; pGKpolyA, polyadenylation sequence; HSV-TK, herpes simplex virus thymidine kinase; pGK-DT-A-pA, diphteria toxin A-chain.

A loxP site flanked puromycin resistance gene was inserted in the adjacent intron 23 bases downstream of position 209 in the wild type α-synuclein gene (the site corresponding to the A53T mutation) and the DSB (see, FIG. 5). For this gene editing strategy, a correct targeting event followed by Cre-recombinase mediated excision of the selection cassette is expected to result in a single base pair change that creates the A53T (G209A) mutation in exon 3 of α-synuclein, with a remaining single loxP site in the following intron (FIG. 5).

The targeting donor construct (Syn-A53T-loxP-pGK-puro-loxP) comprising approximately 600 bp homology on each side of the ZFN targeted site carrying the A53T (G209A) mutation (FIG. 5), together with 4 distinct ZFN pairs were electroporated into two different hESC lines (BG01 and WIBR3).

Southern blot analysis of individual single-cell-derived puromycin-resistant clones using Southern blot probes 5' and 3' external to the donor homology region demonstrated the disruption of the genomic locus and integration of the targeting donor vector with a frequency of at least 25%. Further analysis using an internal probe against the 3' targeting arm of the donor vector and against the ampicillin resistance gene revealed integrations of additional donor-derived vector sequences into the target locus in some clones, presumably via a hybrid homology directed repair (HDR)-end joining based process.

Three out of 336 puromycin resistant clones showed the correct modification of the targeted genomic locus by Southern blot, which was further confirmed by sequencing after Cre-mediated excision of the selection cassette. Two out of the three clones carried a small deletion in the second allele as a result of ZFN mediated gene disruption. The remaining correctly targeted clone with a non-disrupted wild-type allele (WIBR3-SNCA$^{A53T/WT}$) displayed a normal karyotype and maintained a pluripotent state as indicated by the uniform expression of the pluripotency markers OCT4, NANOG, SOX2, Tra-1-60, Tra-1-81 and SSEA4 and the ability to form teratomas comprised of cell types originating from all three developmental germ layers. The stable integration of the transiently transfected ZFNs or the Cre recombinase expressing plasmid was excluded by Southern blot analysis. Furthermore, using an embryoid body (EB) based protocol to induce neural differentiation, we were able to derive efficiently dopaminergic thyrosine hydroxylase (TH) expressing neurons from the targeted WIBR3-SNCA$^{A53T/WT}$ hESC.

It is well established that increased α-synuclein expression levels in patients with genomic α-synuclein duplications and triplications are sufficient to cause PD (see, e.g. Singleton (2003) *Science* 302(5646):841). In order to verify that the loxP site remaining after Cre-mediated excision of the selection cassette does not interfere with the splicing or gene expression of α-synuclein, we differentiated the parental and targeted hESC lines into neurons in order to induce expression of α-synuclein. Mutation analysis RT-PCR confirmed that the levels and ratio of expression of the wild-type and the A53T-mutated transcript in the targeted cell line were similar to those observed in neurons derived from A53T-patient-specific hiPSCs (WIBR-iPS-SNCA$^{A53T(1/ox)}$).

In order to increase the targeting efficiency by reducing non-targeted integrations of the donor vector, as well as integration of donor vector sequences that are outside of the homology arms at the site of ZFN cleavage, we employed a positive-negative selection strategy by incorporating the herpes simplex virus thymidine kinase (HSV-TK) and diphteria toxin A-chain (DT-A) into the vector backbone (FIG. 5).

Using this strategy, 9 out of 41 puromycin- and ganciclovir-resistant colonies resulted in a correctly targeted allele. Four out of these clones had no disruption of the second, wild-type allele and 1 out of the 41 clones resulted in correct targeting and insertion of the A53T (G209A) mutation into both alleles (WIBR3-SNCA$^{A53T/A53T}$). The targeted clones initially identified by Southern blot analysis were confirmed by sequencing of the genomic locus. None of the clones integrated the transiently transfected ZFNs.

Thus, this single step biallelic modification of a disease-relevant locus, only possible as a result of the significantly increased targeting efficiency due to the positive-negative selection strategy, represents a unique tool to study the role of mutant α-synuclein in the absence of the wild-type protein. Individuals homozygous for this mutation have not been described and the study of a homozygous mutant cell may provide new insights into the pathogenesis of PD.

Example 6

Figure 6:
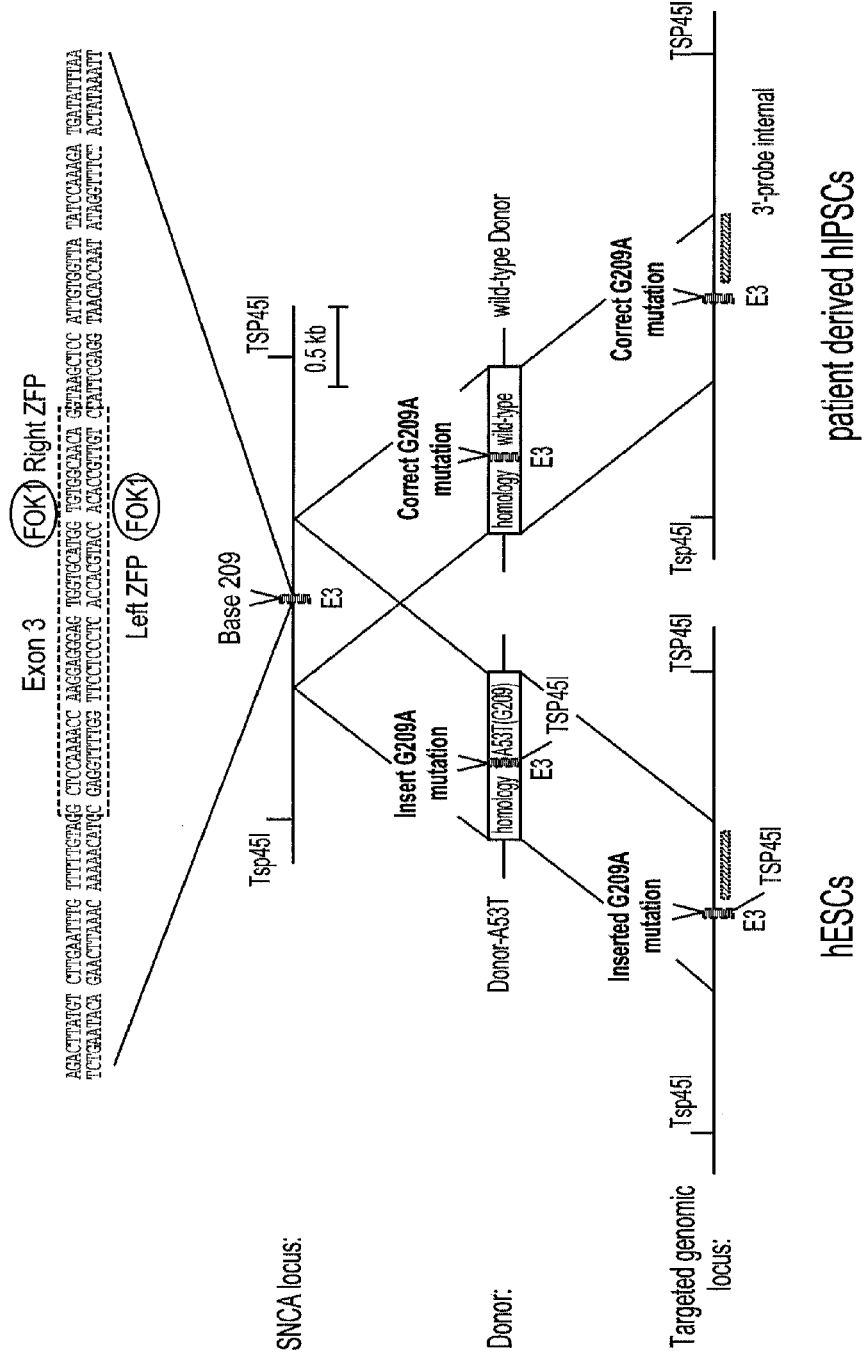
FIG. 6 is a schematic depicting the genomic α-synuclein (SNCA) locus and the targeting strategy showing exons (blue boxes), restriction sites and location of internal southern blot probe (red bars). Enlarged sequence (SEQ ID NO: 52) indicates ZFNs induced cut site at base 209 in exon3 of α-synuclein (red base pair). Shown below is a schematic of donor plasmid design and targeted genomic locus for either insertion (Donor-A53T) or correction (wild-type Donor) of A53T (G209A) α-synuclein mutation. The donor plasmids contain ~1 kb homology to the targeting site.

Introduction of the A53T (G209) Point Mutation into the α-Synuclein Gene without a Selection Marker Genetically-pristine hESCs that contain no exogenous sequences other than the edited base for introducing the disease-causing point mutation were also generated. Given the high gene editing activity of the ZFNs, we constructed a donor vector lacking a selection cassette, including only of ~1 kb homology flanking the ZFN cleavage site and including the A53T (G209A) point mutation in order to insert the mutation in the endogenous wild type α-synuclein locus in hESCs (FIG. 6). The hESC line BGO1 was electroporated with the donor construct together with ZFNs and an eGFP expressing plasmid, which allows transfected cells to be enriched by fluorescence-activated cell sorting (FACS).

Colonies derived from single eGFP expressing cells were screened by Southern blot analysis using an A53T (G209A) allele specific Tsp45I restriction digest. Three out of 240 BGO1 clones showed the A53T (G209A) allele specific restriction pattern, indicative of an accurate genetic alteration event resulting in a A53T (G209A) mutation at the endogenous genomic locus. Further analysis by PCR genotyping and sequencing of the genomic locus confirmed one correctly targeted clone with the expected single base pair change of nucleotide 209 on one allele and an unaffected second allele, resulting in a A53T mutated cell line on a genetic BGO1 background (BGO1-SNCA$^{A53T/WT}$).

The targeted cell line maintained a pluripotent state as shown by the uniform expression of the pluripotency markers OCT4, NANOG, SOX2, Tra-1-60, Tra-1-81 and SSEA4, the ability to form teratomas comprised of cell types originating from all three developmental germ layers and differentiation into dopaminergic neurons in vitro. The stable integration of the ZFNs and GFP expression plasmids was excluded by Southern blot analysis.

These results demonstrate that selection-free, ZFN-driven generation of point mutations was readily achieved in hESCs.

Example 7

Genetic Repair of the A53T (G209) α-Synuclein Mutation in PD Patient-Derived hiPSCs Fibroblasts, obtained from a patient carrying the A53T (G209A) α-synuclein mutation were reprogrammed using previously described doxycycline-inducible and Cre-recombinase excisable lentiviral vectors (see, e.g., Hockemeyer et al. (2008) *Cell Stem Cell.* 3(3):346-53; Soldner et al. (2009) *Cell* 136(5):964-77.

The resulting hiPSCs before (WIBR-iPS-SNCA$^{A53T(2lox)}$) and after Cre-mediated excision of the reprogramming factors (WIBR-iPS-SNCA$^{A53T(11ox)}$) displayed all basic properties of pluripotent cells as indicated by the uniform expression of the pluripotency marker proteins OCT4, NANOG, SOX2, Tra-1-60, Tra-1-81 and SSEA4, the ability to form teratomas comprised of cell types originating from all three developmental germ layers and a normal karyotype. Sequencing of the genomic α-synuclein locus confirmed the A53T (G209A) mutation in the patient derived hiPSCs. Furthermore, the cells were shown to differentiate into thyrosine-hydroxylase expressing dopaminergic neurons, the cell type primarily affected in PD.

In order to genetically repair the A53T (G209) mutation in the PD patient-derived hiPSCs, we employed a similar selection-free targeting strategy as described above for hESCs with the only difference of using a wild-type sequence containing donor vector.

Six out of 240 WIBR-iPS-SNCA$^{A53T}$ clones demonstrated the loss of the A53T specific Tsp45I restriction site by Southern blot screening, which is either the result of a ZFN-induced DSB followed by non-homologous error-prone end joining or HDR based correction of the allele. Further analysis by PCR genotyping and sequencing of the genomic locus confirmed one correctly repaired patient-derived hiPSC lines with the expected single base pair change of nucleotide 209 of α-synuclein.

Finally, to prevent uncontrollable effects from residual expression of the reprogramming transgenes (see, e.g., Soldner, supra), we excised the reprogramming vectors from the corrected patient derived hiPCs (WIBR-iPS-SNCA$^{A53T-Corr}$), which subsequently displayed a normal karyotype, maintained a pluripotent state as indicated by the uniform expression of the pluripotency markers OCT4, NANOG, SOX2, Tra-1-60, Tra-1-81 and SSEA4 and the ability to form teratomas comprised of cell types originating from all three developmental germ layers. Stable integration of ZFNs, Cre recombinase and GFP expression plasmids was excluded by Southern blot analysis. The genetic repair of the A53T mutation in the patient-derived hiPSCs did not compromise the ability to differentiate into TH expressing dopaminergic neurons.

To further validate accurate editing of the α-synuclein locus in the repaired patient-derived hiPSC line (WIBR-iPS-SNCA$^{A53T-Corr}$), we performed mutation analysis RT-PCR of α-synuclein after neuronal differentiation which confirmed the loss of expression of the mutated A53T(G209A) transcript.

Example 8

Additional Genetic Alterations in Engineered ESCs and iPSCs

A potential limitation of ZFN mediated genome editing is the induction of off-target DNA strand breaks at related sequences other than the intended target site. To examine off-target modifications in the targeted cell lines we initially determined the DNA binding specificity for each ZFN employed in this study by SELEX analysis as described previously, for example in Hockemeyer et al. (2009), supra; Perez et al. (2008), supra). This allows for the identification of the most probable off-target cleavage sites genome-wide. A Surveyor endonuclease (Cel-1) assay was subsequently performed to reveal any potential nonhomologous end joining (NHEJ)-mediated indels for the top 12 putative off-target sites in the WIBR3-SNCA$^{A53T/WT}$-2, WIBR3-SNCA$^{A53T/WT}$-3 and WLBR3-SNCA-$^{A53T/A53T}$ lines and the top 38 putative off-target sites (representing candidate off target sites for the L1/R1 ZFN heterodimerization, as well as L1 and R1 homodimerization sites) for WIBR3-iPS-SNCA$^{A53T/corr}$, BGO1-SNCA$^{A53T/WT}$ and WIBR3-SNCA$^{A53T/WT}$-1. No evidence of off-target cleavage at any of the examined loci was found.

It is well established that prolonged culture of hESCs can lead to adaption such as increased growth rate, reduced apoptosis and the acquisition of chromosomal abnormalities such as copy number variations (CNVs). See, e.g., Narva et al. (2010) Nat Biotechnol. 28(4):371-7). More recently, it has been proposed that the reprogramming process itself compromises the genomic integrity and leads to the accumulating of CNVs and somatic mutations. See, e.g. Gore et al. (2011) Nature 471(7336):63-67; Hussein et al. (2011) Nature 471 (7336):58-62. Although all our tested cell lines showed a normal karyotype after genome editing as determined by conventional karyotyping, the low resolution of this technology excludes the detection of smaller CNVs, which are considered a major source for human genome variability and particularly important in the context of genome editing. Such genetic changes involve the induction of DNA double strand breaks and clonal events, which are thought to increase the chance for additional genomic alterations. We therefore performed high-resolution genome wide CNV analysis using an Affymetrix SNP 6.0 array as described previously in Hussein et al., supra and Narva et al., supra on 3 pairs of isogenic parental and genetically modified cell lines.

We identified on average 77 CNVs with an average size of 158 kb per cell line. For human ES cell lines this is slightly higher as described previously and may be due technical variability such as low sample or the higher passage numbers (between Passage P25 and P60 for hESCs and P22 and P40 for hiPSCs) of the cell lines used in this study. 63% of the identified CNVs (number and total genomic area) overlapped between isogenic pairs using pairwise comparison before and after ZFN mediated genome modification. In contrast, we observed only 35% overlap of CNVs between genetically unrelated samples. This degree of overlap is comparable to previously published hESC data comparing identical cell lines at different passage numbers. See, e.g., Narva et al., supra. Furthermore, comparing average number and total genome area of CNVs before and after ZFN mediated gene targeting did not reveal any additional increase other than that observed during regular hESCs in culture.

Thus, our analysis confirms that hESCs and hiPSCs contain a higher number of CNVs than the normal human genome, probably acquired during the reprogramming process and prolonged cell culture. We conclude that the Cre-recombinase mediated excision of the reprogramming factors and ZFN mediated genome editing did not substantially increase the level of genomic alterations.

To further validate that the genome editing approach did not induce major genetic or epigenetic alterations, which would result in aberrant gene expression profiles, we performed whole genome expression analysis of undifferentiated pairs of parental and genetically modified cell lines. Despite very similar gene expression of all pluripotent cell lines hierarchical cluster analysis suggests that the influence of genetic background on gene expression is more significant than the genome editing, since gene expression patterns of pairs of parental and genome edited cell lines are more closely correlated than to genetically independent cell lines (see Soldner et al. (2011) Cell 146(2): 318-331).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger nuclease (ZFN) fusion protein comprising a cleavage domain and a zinc-finger protein (ZFP) that binds to a target site in a leucine rich repeat kinase 2 (LRRK2) or α-synuclein (SCNA) gene in a genome, wherein the ZFP comprises 5 or 6 engineered zinc-finger binding domains, each zinc finger domain comprising a recognition helix region designated F1 to F5 or F1 to F6, wherein the zinc finger protein comprises the recognition helix regions as shown in a single row of Table 2 or Table 4 and further wherein the target site is selected from the group consisting of SEQ ID NO:17, SEQ ID NO:18, SEQ ID NO:46, SEQ ID NO:36 and SEQ ID NO:37.

2. A kit comprising a ZFN according to claim 1 and instructions for cleaving a LRRK2 or a SCNA gene.

* * * * *